United States Patent [19]
Hunter et al.

[11] Patent Number: 5,837,837
[45] Date of Patent: Nov. 17, 1998

[54] NUCLEIC ACIDS MOLECULES ENCODING CASPASE-8H AND CASPASE-8I

[75] Inventors: John J. Hunter, Cambridge; Andrew W. Shyjan, Nahant; Grace H. W. Wong, Brookline, all of Mass.

[73] Assignee: Millennium Pharmaceuticals, Inc., Cambridge, Mass.

[21] Appl. No.: 807,200

[22] Filed: Feb. 27, 1997

[51] Int. Cl.[6] .......................... C07H 21/02; A61K 38/00; C07K 1/00
[52] U.S. Cl. .......................... 536/23.1; 530/300; 530/350
[58] Field of Search .......................... 536/23.1; 530/350; 435/172.3, 69.1, 325; 424/93.2

[56] References Cited

PUBLICATIONS

Chinnaiyan et al., Cell 81:505–512, 1995.
Cotman et al., "A potential role for apoptosis in neurodengeneration and Alzheimer's disease" Mol. Neurobiol. 10(1):19–45, 1995.
Boldin et al., "Involvement of MACH, a Novel MORT1/FADD—Interacting Protease, in Fas/APO–1–and TNF . . . " Cell 85:803–815, 1996.
Johnson et al., "Neuronal apoptosis: Current understanding of molecular mechanisms and potential role in ischemic brain injury" J. Neurotrauma 12(5):843–52, 1995.
McDonnell et al., "Implications of apoptotic cell death regulation in cancer therapy" Semin. Cancer Biol. 6(1):53–60, 1995.
Muzio et al., "Flice, A novel FADD–Homogous ICE/CED–3–like Protease, is recruited to the CD95 . . . " Cell 85:817–827, 1996.
Thompson, "Apoptosis in the Pathogenesis and Treatment of Disease" Science 267:1456–1462, 1995.
Sambrook et al., 1989, "Expression of cloned genes in cultured mammalian cells", in *Molecular Cloning : A Laboratory Manual*, Sambrook et al., eds., Cold Spring Harbor Laboratory Press, pp. 16.1–16.31.
Sambrook et al., 1989, "Expression of cloned genes in cultured mammalian cells", in *Molecular Cloning: A Laboratory Manual*, Sambrook et al., eds., Cold Spring Harbor Laboratory Press, pp. 17.1–17.17.
Majors, J., 1992, "Retroviral vectors–strategies and applications", Sem. Virol. 3:285–295.

*Primary Examiner*—Jeffrey Stucker
*Assistant Examiner*—Jeffrey S. Parkin
*Attorney, Agent, or Firm*—Fish & Richardson, P.C.

[57] ABSTRACT

The present invention concerns the Caspase-8h gene and the Caspase-8i gene. The Caspase-8h gene encodes a 220 amino acid polypeptide having two FADD death effector domains. The Caspase-8i gene encodes an 81 amino acid polypeptide having one FADD death effector domain. The invention encompasses nucleic acid molecules encoding Caspase-8h or Caspase-8i, vectors containing these nucleic acid molecules, and cells harboring such vectors.

18 Claims, 5 Drawing Sheets

```
ATG GAC TTC AGC AGA AAT CTT TAT GAT ATT GGG GAA CAA CTG    42
GAC AGT GAA GAT CTG GCC TCC CTC AAG TTC CTG AGC CTG GAC    84
TAC ATT CCG CAA AGG AAG CAA GAA CCC ATC AAG GAT GCC TTG   126
ATG TTA TTC CAG AGA CTC CAG GAA AAG AGA ATG TTG GAG GAA   168
AGC AAT CTG TCC TTC CTG AAG GAG CTG CTC TTC CGA ATT AAT   210
AGA CTG GAT TTG CTG ATT ACC TAC CTA AAC ACT AGA AAG GAG   252
GAG ATG GAA AGG GAA CTT CAG ACA CCA GGC AGG GCT CAA ATT   294
TCT GCC TAC AGG GTC ATG CTC TAT CAG ATT TCA GAA GAA GTG   336
AGC AGA TCA GAA TTG AGG TCT TTT AAG TTT CTT TTG CAA GAG   378
GAA ATC TCC AAA TGC AAA CTG GAT GAT GAC ATG AAC CTG CTG   420
GAT ATT TTC ATA GAG ATG GAG AAG AGG GTC ATC CTG GGA GAA   462
GGA AAG TTG GAC ATC CTG AAA AGA GTC TGT GCC CAA ATC AAC   504
AAG AGC CTG CTG AAG ATA ATC AAC GAC TAT GAA GAA TTC AGC   546
AAA GAC TTT GGA CAA AGT TTA CCA AAT GAA AAG CAA ACC TCG   588
GGG ATA CTG TCT GAT CAT CAA CAA TCA CAA TTT TGC AAA AGC   630
ACG GGA GAA AGT GCC CAA ACT TCA CAG CAT TAG GGA CAG GAA   672
TGG AAC ACA CTT GGA TGC AGG GGC TTT GAC CAC GAC CTT TGA   714
AGA GCT TCA TTT TGA GAT CAA GCC CCA CGA TGA CTG CAC AGT   756
AGA GCA AAT CTA TGA GAT TTT GAA AAT CTA CCA ACT CAT GGA   798
CCA CAG TAA CAT GGA CTG CTT CAT CTG CTG TAT CCT CTC CCA   840
TGG AGA CAA GGG CAT CAT CTA TGG CAC TGA TGG ACA GGA GGC   882
CCC CAT CTA TGA GCT GAC ATC TCA GTT CAC TGG TTT GAA GTG   924
CCC TTC CCT TGC TGG AAA ACC CAA AGT GTT TTT TAT TCA GGC   966
TTG TCA GGG GGA TAA CTA CCA GAA AGG TAT ACC TGT TGA GAC  1008
TGA TTC AGA GGA GCA ACC CTA TTT AGA AAT GGA TTT ATC ATC  1050
ACC TCA AAC GAG ATA TAT CCC GGA TGA GGC TGA CTT TCT GCT  1092
GGG GAT GGC CAC TGT GAA TAA CTG TGT TCT ACC GAA ACC CTG  1134
TGC AGA GGG AAC CTG GTA CAT CCA GTC ACT TTG CCA GAG CCT  1176
GAG AGA GCG ATG TCC TCG AGG CGA TGA TAT TCT CAC CAT CCT  1218
GAC TGA AGT GAA CTA TGA AGT AAG CAA CAA GGA TGA CAA GAA  1260
AAA CAT GGG GAA ACA GAT GCC TCA GCC TAC TTT CAC ACT AAG  1302
AAA AAA ACT TGT CTT CCC TTC TGA TTG A 1330 (SEQ. ID. NO: 1)
```

FIG. 2

```
MDFSRNLYDIGEQLDSEDLASLKFLSLDYIPQRKQEPIKD   40
ALMLFQRLQEKRMLEESNLSFLKELLFRINRLDLLITYLN   80
TRKEEMERELQTPGRAQISAYRVMLYQISEEVSRSELRSF  120
KFLLQEEISKCKLDDDMNLLDIFIEMEKRVILGEGKLDIL  160
KRVCAQINKSLLKIINDYEEFSKDFGQSLPNEKQTSGILS  200
DHQQSQFCKSTGESAQTSQH.  221 (SEQ. ID. NO.: 2)
```

FIG. 3

```
ATG GAC TTC AGC AGA AAT CTT TAT GAT ATT GGG GAA CAA CTG   42
GAC AGT GAA GAT CTG GCC TCC CTC AAG TTC CTG AGC CTG GAC   84
TAC ATT CCG CAA AGG AAG CAA GAA CCC ATC AAG GAT GCC TTG  126
ATG TTA TTC CAG AGA CTC CAG GAA AAG AGA ATG TTG GAG GAA  168
AGC AAT CTG TCC TTC CTG AAG GAG CTG CTC TTC CGA ATT AAT  210
AGA CTG GAT TTG CTG ATT ACC TAC CTA AAC ACT TAA GTT TCT  252
TTT GCA AGA GGA AAT CTC CAA ATG CTC TAT CAG ATT TCA GAA  294
GAA GTG AGC AGA TCA GAA TTG AGT TTA CCC TGA AAA GAG TCT  336
GTG CCC AAA TCA ACA AGA GCC TGC TGA AGA TAA TCA ACG ACT  378
ATG AAG AAT TCA GCA AAG AGA GAA GCA GCA GCC TTG AAG GAA  420
GTC CTG ATG AAT TTT CAA ATG GGG AGG AGT TGT GTG GGG TAA  462
TGA CAA TCT CGG ACT CTC CAA GAG AAC AGG ATA GTG AAT CAC  504
AGA CTT TGG ACA AAG TTT ACC AAA TGA AAA GCA AAC CTC GGG  546
GAT ACT GTC TGA TCA TCA ACA ATC ACA ATT TTG CAA AAG CAC  588
GGG AGA AAG TGC CCA AAC TTC ACA GCA TTA GGG ACA GGA ATG  630
GAA CAC ACT TGG ATG CAG GGG CTT TGA CCA CGA CCT TTG AAG  672
AGC TTC ATT TTG AGA TCA AGC CCC ACG ATG ACT GCA CAG TAG  714
AGC AAA TCT ATG AGA TTT TGA AAA TCT ACC AAC TCA TGG ACC  756
ACA GTA ACA TGG ACT GCT TCA TCT GCT GTA TCC TCT CCC ATG  798
GAG ACA AGG GCA TCA TCT ATG GCA CTG ATG GAC AGG AGG CCC  840
CCA TCT ATG AGC TGA CAT CTC AGT TCA CTG GTT TGA AGT GCC  882
CTT CCC TTG CTG GAA AAC CCA AAG TGT TTT TTA TTC AGG CTT  924
GTC AGG GGA ATA ACT ACC AGA AAG TAC CTG TTG AGA CTG      966
ATT CAG AGG AGC AAC CCT ATT TAG AAA TGG ATT TAT CAT CAC 1008
CTC AAA CGA GAT ATA TCC GGA TGA GGC TGA CTT TCT GCT GG  1050
GGA TGG CCA CTG TGA ATA ACT GTG TTT CCT ACC GAA ACC CTG 1092
CAG AGG GAA CCT GGT ACA TCC AGT CAC TTT GCC AGA GCC TGA 1134
GAG AGC GAT GTC CTC GAG GCG ATG ATA TTC TCA CCA TCC TGA 1176
CTG AAG TGA ACT ATG AAG TAA GCA ACA AGG ATG ACA AGA AAA 1218
ACA TGG GGA AAC AGA TGC CTC AGC CTA CTT TCA CAC TAA GAA 1260
AAA AAC TTG TCT TCC CTT CTG ATT GA 1286 (SEQ. ID. NO.: 3)
```

FIG. 4

```
MDFSRNLYDIGEQLDSEDLASLKFLSLDYIPQRKQEPIKD 40
ALMLFQRLQEKRMLEESNLSFLKELLFRINRLDLLITYLN 80
T. 82 (SEQ. ID. NO.: 4)
```

FIG. 5

```
ATG GAC TTC AGC AGA AAT CTT TAT GAT ATT GGG GAA CAA CTG    42
GAC AGT GAA GAT CTG GCC TCC CTC AAG TTC CTG AGC CTG GAC    84
TAC ATT CCG CAA AGG AAG CAA GAA CCC ATC AAG GAT GCC TTG   126
ATG TTA TTC CAG AGA CTC CAG GAA AAG AGA ATG TTG GAG GAA   168
AGC AAT CTG TCC TTC CTG AAG GAG CTG CTC TTC CGA ATT AAT   210
AGA CTG GAT TTG CTG ATT ACC TAC CTA AAC ACT AGA AAG GAG   252
GAG ATG GAA AGG GAA CTT CAG ACA CCA GGC AGG GCT CAA ATT   294
TCT GCC TAC AGG GTC ATG CTC TAT CAG ATT TCA GAA GAA GTG   336
AGC AGA TCA GAA TTG AGG TCT TTT AAG TTT CTT TTG CAA GAG   378
GAA ATC TCC AAA TGC AAA CTG GAT GAT GAC ATG AAC CTG CTG   420
GAT ATT TTC ATA GAG ATG GAG AAG AGG GTC ATC CTG GGA GAA   462
GGA AAG TTG GAC ATC CTG AAA AGA GTC TGT GCC CAA ATC AAC   504
AAG AGC CTG CTG AAG ATA ATC AAC GAC TAT GAA GAA TTC AGC   546
AAA GAG AGA AGC AGC AGC CTT GAA GGA AGT CCT GAT GAA TTT   588
TCA AAT GGG GAG GAG TTG TGT GGG GTA ATG ACA ATC TCG GAC   630
TCT CCA AGA GAA CAG GAT AGT GAA TCA CAG ACT TTG GAC AAA   672
GTT TAC CAA ATG AAA AGC AAA CCT CGG GGA TAC TGT CTG ATC   714
ATC AAC AAT CAC AAT TTT GCA AAA GCA CGG GAG AAA GTG CCC   756
AAA CTT CAC AGC ATT AGG GAC AGG AAT GGA ACA CAC TTG GAT   798
GCA GGG GCT TTG ACC ACG ACC TTT GAA GAG CTT CAT TTT GAG   840
ATC AAG CCC CAC GAT GAC TGC ACA GTA GAG CAA ATC TAT GAG   882
ATT TTG AAA ATC TAC CAA CTC ATG GAC CAC AGT AAC ATG GAC   924
TGC TTC ATC TGC TGT ATC CTC TCC CAT GGA GAC AAG GGC ATC   966
ATC TAT GGC ACT GAT GGA CAG GAG CCC CCC ATC TAT GAG CTG  1008
ACA TCT CAG TTC ACT GGT TTG AAG TGC CCT TCC CTT GCT GGA  1050
AAA CCC AAA GTG TTT TTT ATT CAG GCT TGT CAG GGG GAT AAC  1092
TAC CAG AAA GGT ATA CCT GTT GAG ACT GAT TCA GAG GAG CAA  1134
CCC TAT TTA GAA ATG GAT TTA TCA TCA CCT CAA ACG AGA TAT  1176
ATC CCG GAT GAG GCT GAC TTT CTG CTG GGG ATG GCC ACT GTG  1218
AAT AAC TGT GTT TCC TAC CGA AAC CCT GCA GAG GGA ACC TGG  1260
TAC ATC CAG TCA CTT TGC AGA GCT GAG AGA GAC TGT CCT  1302
CGA GGC GAT GAT ATT CTC ACC ATC CTG ACT GAA GTG AAC TAT  1344
GAA GTA AGC AAC AAG GAT GAC AAG AAA AAC ATG GGG AAA CAG  1386
ATG CCT CAG CCT ACT TTC ACA CTA AGA AAA AAA CTT GTC TTC  1428
CCT TCT GAT TGA    1440 (SEQ. ID. NO.: 11)
```

FIG. 6

```
MDFSRNLYDIGEQLDSEDLASLKFLSLDYIPQRKQEPIKD      40
ALMLFQRLQEKRMLEESNLSFLKELLFRINRLDLLITYLN      80
TRKEEMERELQTPGRAQISAYRVMLYQISEEVSRSELRSF     120
KFLLQEEISKCKLDDDMNLLDIFIEMEKRVILGEGKLDIL     160
KRVCAQINKSLLKIINDYEEFSKERSSSLEGSPDEFSNGE     200
ELCGVMTISDSPREQDSESQTLDKVYQMKSKPRGYCLIIN     240
NHNFAKAREKVPKLHSIRDRNGTHLDAGALTTTFEELHFE     280
IKPHDDCTVEQIYEILKIYQLMDHSNMDCFICCILSHGDK     320
GIIYGTDGQEPPIYELTSQFTGLKCPSLAGKPKVFFIQAC     360
QGDNYQKGIPVETDSEEQPYLEMDLSSPQTRYIPDEADFL     400
LGMATVNNCVSYRNPAEGTWYIQSLCQSLRERCPRGDDIL     440
TILTEVNYEVSNKDDKKNMGKQMPQPTFTLRKKLVFPSD.     480
(SEQ. ID. NO.: 12)
```

FIG. 7

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1330 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
ATGGACTTCA   GCAGAAATCT   TTATGATATT   GGGGAACAAC   TGGACAGTGA   AGATCTGGCC        60
TCCCTCAAGT   TCCTGAGCCT   GGACTACATT   CCGCAAAGGA   AGCAAGAACC   CATCAAGGAT       120
```

```
GCCTTGATGT  TATTCCAGAG  ACTCCAGGAA  AAGAGAATGT  TGGAGGAAAG  CAATCTGTCC    180

TTCCTGAAGG  AGCTGCTCTT  CCGAATTAAT  AGACTGGATT  TGCTGATTAC  CTACCTAAAC    240

ACTAGAAAGG  AGGAGATGGA  AAGGGAACTT  CAGACACCAG  GCAGGGCTCA  AATTTCTGCC    300

TACAGGGTCA  TGCTCTATCA  GATTTCAGAA  GAAGTGAGCA  GATCAGAATT  GAGGTCTTTT    360

AAGTTTCTTT  TGCAAGAGGA  AATCTCCAAA  TGCAAACTGG  ATGATGACAT  GAACCTGCTG    420

GATATTTTCA  TAGAGATGGA  GAAGAGGGTC  ATCCTGGGAG  AAGGAAAGTT  GGACATCCTG    480

AAAAGAGTCT  GTGCCCAAAT  CAACAAGAGC  CTGCTGAAGA  TAATCAACGA  CTATGAAGAA    540

TTCAGCAAAG  ACTTTGGACA  AAGTTTACCA  AATGAAAAGC  AAACCTCGGG  GATACTGTCT    600

GATCATCAAC  AATCACAATT  TTGCAAAAGC  ACGGGAGAAA  GTGCCCAAAC  TTCACAGCAT    660

TAGGGACAGG  AATGGAACAC  ACTTGGATGC  AGGGGCTTTG  ACCACGACCT  TGAAGAGCT     720

TCATTTTGAG  ATCAAGCCCC  ACGATGACTG  CACAGTAGAG  CAAATCTATG  AGATTTTGAA    780

AATCTACCAA  CTCATGGACC  ACAGTAACAT  GGACTGCTTC  ATCTGCTGTA  TCCTCTCCCA    840

TGGAGACAAG  GGCATCATCT  ATGGCACTGA  TGGACAGGAG  GCCCCATCT   ATGAGCTGAC    900

ATCTCAGTTC  ACTGGTTTGA  AGTGCCCTTC  CCTTGCTGGA  AAACCCAAAG  TGTTTTTTAT    960

TCAGGCTTGT  CAGGGGGATA  ACTACCAGAA  AGGTATACCT  GTTGAGACTG  ATTCAGAGGA   1020

GCAACCCTAT  TTAGAAATGG  ATTTATCATC  ACCTCAAACG  AGATATATCC  CGGATGAGGC   1080

TGACTTTCTG  CTGGGGATGG  CCACTGTGAA  TAACTGTGTT  TCCTACCGAA  ACCCTGCAGA   1140

GGGAACCTGG  TACATCCAGT  CACTTTGCCA  GAGCCTGAGA  GAGCGATGTC  CTCGAGGCGA   1200

TGATATTCTC  ACCATCCTGA  CTGAAGTGAA  CTATGAAGTA  AGCAACAAGG  ATGACAAGAA   1260

AAACATGGGG  AAACAGATGC  CTCAGCCTAC  TTTCACACTA  AGAAAAAAAC  TTGTCTTCCC   1320

TTCTGATTGA                                                              1330
```

( 2 ) INFORMATION FOR SEQ ID NO:2:

( i ) SEQUENCE CHARACTERISTICS:
        ( A ) LENGTH: 220 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asp  Phe  Ser  Arg  Asn  Leu  Tyr  Asp  Ile  Gly  Glu  Gln  Leu  Asp  Ser
 1              5                        10                       15

Glu  Asp  Leu  Ala  Ser  Leu  Lys  Phe  Leu  Ser  Leu  Asp  Tyr  Ile  Pro  Gln
                20                       25                       30

Arg  Lys  Gln  Glu  Pro  Ile  Lys  Asp  Ala  Leu  Met  Leu  Phe  Gln  Arg  Leu
           35                       40                       45

Gln  Glu  Lys  Arg  Met  Leu  Glu  Glu  Ser  Asn  Leu  Ser  Phe  Leu  Lys  Glu
      50                       55                       60

Leu  Leu  Phe  Arg  Ile  Asn  Arg  Leu  Asp  Leu  Leu  Ile  Thr  Tyr  Leu  Asn
65                       70                       75                       80

Thr  Arg  Lys  Glu  Glu  Met  Glu  Arg  Glu  Leu  Gln  Thr  Pro  Gly  Arg  Ala
                     85                       90                       95

Gln  Ile  Ser  Ala  Tyr  Arg  Val  Met  Leu  Tyr  Gln  Ile  Ser  Glu  Glu  Val
                100                      105                      110

Ser  Arg  Ser  Glu  Leu  Arg  Ser  Phe  Lys  Phe  Leu  Leu  Gln  Glu  Glu  Ile
           115                      120                      125

Ser  Lys  Cys  Lys  Leu  Asp  Asp  Asp  Met  Asn  Leu  Leu  Asp  Ile  Phe  Ile
```

|     |     |     | 130 |     |     |     |     | 135 |     |     |     |     | 140 |     |     |
| --- | --- | --- | --- | --- | --- | --- | --- | --- | --- | --- | --- | --- | --- | --- | --- |

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Asp Phe Gly Gln Ser Leu Pro Asn Glu
            180                 185                 190

Lys Gln Thr Ser Gly Ile Leu Ser Asp His Gln Gln Ser Gln Phe Cys
        195                 200                 205

Lys Ser Thr Gly Glu Ser Ala Gln Thr Ser Gln His
        210                 215                 220

(2) INFORMATION FOR SEQ ID NO:3:

(i) SEQUENCE CHARACTERISTICS:
        (A) LENGTH: 1286 base pairs
        (B) TYPE: nucleic acid
        (C) STRANDEDNESS: single
        (D) TOPOLOGY: linear (xi) SEQUENCE DESCRIPTION: SEQ ID NO:3:

| | | | | | |
|---|---|---|---|---|---|
| ATGGACTTCA | GCAGAAATCT | TTATGATATT | GGGGAACAAC | TGGACAGTGA | AGATCTGGCC | 60 |
| TCCCTCAAGT | TCCTGAGCCT | GGACTACATT | CCGCAAAGGA | AGCAAGAACC | CATCAAGGAT | 120 |
| GCCTTGATGT | TATTCCAGAG | ACTCCAGGAA | AAGAGAATGT | GGAGGAAAG | CAATCTGTCC | 180 |
| TTCCTGAAGG | AGCTGCTCTT | CCGAATTAAT | AGACTGGATT | TGCTGATTAC | CTACCTAAAC | 240 |
| ACTTAAGTTT | CTTTTGCAAG | AGGAAATCTC | CAAATGCTCT | ATCAGATTTC | AGAAGAAGTG | 300 |
| AGCAGATCAG | AATTGAGTTT | ACCCTGAAAA | GAGTCTGTGC | CCAAATCAAC | AAGAGCCTGC | 360 |
| TGAAGATAAT | CAACGACTAT | GAAGAATTCA | GCAAAGAGAG | AAGCAGCAGC | CTTGAAGGAA | 420 |
| GTCCTGATGA | ATTTTCAAAT | GGGGAGGAGT | TGTGTGGGGT | AATGACAATC | TCGGACTCTC | 480 |
| CAAGAGAACA | GGATAGTGAA | TCACAGACTT | TGGACAAAGT | TTACCAAATG | AAAAGCAAAC | 540 |
| CTCGGGGATA | CTGTCTGATC | ATCAACAATC | ACAATTTTGC | AAAAGCACGG | AGAAAGTGC | 600 |
| CCAAACTTCA | CAGCATTAGG | GACAGGAATG | GAACACACTT | GGATGCAGGG | GCTTTGACCA | 660 |
| CGACCTTTGA | AGAGCTTCAT | TTTGAGATCA | AGCCCCACGA | TGACTGCACA | GTAGAGCAAA | 720 |
| TCTATGAGAT | TTTGAAAATC | TACCAACTCA | TGGACCACAG | TAACATGGAC | TGCTTCATCT | 780 |
| GCTGTATCCT | CTCCCATGGA | GACAAGGGCA | TCATCTATGG | CACTGATGGA | CAGGAGGCCC | 840 |
| CCATCTATGA | GCTGACATCT | CAGTTCACTG | GTTTGAAGTG | CCCTTCCCTT | GCTGGAAAAC | 900 |
| CCAAAGTGTT | TTTTATTCAG | GCTTGTCAGG | GGGATAACTA | CCAGAAAGGT | ATACCTGTTG | 960 |
| AGACTGATTC | AGAGGAGCAA | CCCTATTTAG | AAATGGATTT | ATCATCACCT | CAAACGAGAT | 1020 |
| ATATCCCGGA | TGAGGCTGAC | TTTCTGCTGG | GGATGGCCAC | TGTGAATAAC | TGTGTTTCCT | 1080 |
| ACCGAAACCC | TGCAGAGGGA | ACCTGGTACA | TCCAGTCACT | TTGCCAGAGC | CTGAGAGAGC | 1140 |
| GATGTCCTCG | AGGCGATGAT | ATTCTCACCA | TCCTGACTGA | AGTGAACTAT | GAAGTAAGCA | 1200 |
| ACAAGGATGA | CAAGAAAAAC | ATGGGGAAAC | AGATGCCTCA | GCCTACTTTC | ACACTAAGAA | 1260 |
| AAAAACTTGT | CTTCCCTTCT | GATTGA | | | | 1286 |

(2) INFORMATION FOR SEQ ID NO:4:

(i) SEQUENCE CHARACTERISTICS:
        (A) LENGTH: 81 amino acids
        (B) TYPE: amino acid
        (D) TOPOLOGY: linear ( i i ) MOLECULE TYPE: protein ( x i ) SEQUENCE DESCRIPTION: SEQ ID NO:4:

| Met | Asp | Phe | Ser | Arg | Asn | Leu | Tyr | Asp | Ile | Gly | Glu | Gln | Leu | Asp | Ser |
|---|---|---|---|---|---|---|---|---|---|---|---|---|---|---|---|
| 1 | | | | 5 | | | | | 10 | | | | | 15 | |

| Glu | Asp | Leu | Ala | Ser | Leu | Lys | Phe | Leu | Ser | Leu | Asp | Tyr | Ile | Pro | Gln |
|---|---|---|---|---|---|---|---|---|---|---|---|---|---|---|---|
| | | | | 20 | | | | | 25 | | | | | 30 | |

| Arg | Lys | Gln | Glu | Pro | Ile | Lys | Asp | Ala | Leu | Met | Leu | Phe | Gln | Arg | Leu |
|---|---|---|---|---|---|---|---|---|---|---|---|---|---|---|---|
| | | 35 | | | | | 40 | | | | | 45 | | | |

| Gln | Glu | Lys | Arg | Met | Leu | Glu | Glu | Ser | Asn | Leu | Ser | Phe | Leu | Lys | Glu |
|---|---|---|---|---|---|---|---|---|---|---|---|---|---|---|---|
| | 50 | | | | | 55 | | | | | 60 | | | | |

| Leu | Leu | Phe | Arg | Ile | Asn | Arg | Leu | Asp | Leu | Leu | Ile | Thr | Tyr | Leu | Asn |
|---|---|---|---|---|---|---|---|---|---|---|---|---|---|---|---|
| 65 | | | | | 70 | | | | | 75 | | | | | 80 |

Thr ( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

ATGGACTTCA GCAGAAATCT TTATG　　　　　　　　　　　　　　　　　　　　25

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TCAATCAGAA GGGAAGACAA GTTTT　　　　　　　　　　　　　　　　　　　　25

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TTTGTCCAAA GTCTTTGCTG AATT　　　　　　　　　　　　　　　　　　　　　24

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TGGAGATTTC CTCTTGCAAA AGAAACTTA　　　　　　　　　　　　　　　　　　29

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single (D) TOPOLOGY: linear (xi) SEQUENCE DESCRIPTION: SEQ ID NO:9:

GATAGAGCAT TTGGAGATTT CC 22

(2) INFORMATION FOR SEQ ID NO:10:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:10:

CTTTTCAGGG TAAACTCAAT TCTG 24

(2) INFORMATION FOR SEQ ID NO:11:

(i) SEQUENCE CHARACTERISTICS:
(A) LENGTH: 1440 base pairs
(B) TYPE: nucleic acid
(C) STRANDEDNESS: single
(D) TOPOLOGY: linear (xi) SEQUENCE DESCRIPTION: SEQ ID NO:11:

| | | | | | |
|---|---|---|---|---|---|
| ATGGACTTCA | GCAGAAATCT | TTATGATATT | GGGGAACAAC | TGGACAGTGA | AGATCTGGCC | 60 |
| TCCCTCAAGT | TCCTGAGCCT | GGACTACATT | CCGCAAAGGA | AGCAAGAACC | CATCAAGGAT | 120 |
| GCCTTGATGT | TATTCCAGAG | ACTCCAGGAA | AAGAGAATGT | TGGAGGAAAG | CAATCTGTCC | 180 |
| TTCCTGAAGG | AGCTGCTCTT | CCGAATTAAT | AGACTGGATT | TGCTGATTAC | CTACCTAAAC | 240 |
| ACTAGAAAGG | AGGAGATGGA | AAGGGAACTT | CAGACACCAG | GCAGGGCTCA | AATTTCTGCC | 300 |
| TACAGGGTCA | TGCTCTATCA | GATTTCAGAA | GAAGTGAGCA | GATCAGAATT | GAGGTCTTTT | 360 |
| AAGTTTCTTT | TGCAAGAGGA | AATCTCCAAA | TGCAAACTGG | ATGATGACAT | GAACCTGCTG | 420 |
| GATATTTTCA | TAGAGATGGA | GAAGAGGGTC | ATCCTGGGAG | AAGGAAAGTT | GGACATCCTG | 480 |
| AAAAGAGTCT | GTGCCCAAAT | CAACAAGAGC | CTGCTGAAGA | TAATCAACGA | CTATGAAGAA | 540 |
| TTCAGCAAAG | AGAGAAGCAG | CAGCCTTGAA | GGAAGTCCTG | ATGAATTTTC | AAATGGGGAG | 600 |
| GAGTTGTGTG | GGGTAATGAC | AATCTCGGAC | TCTCCAAGAG | AACAGGATAG | TGAATCACAG | 660 |
| ACTTTGGACA | AAGTTTACCA | AATGAAAAGC | AAACCTCGGG | GATACTGTCT | GATCATCAAC | 720 |
| AATCACAATT | TTGCAAAAGC | ACGGGAGAAA | GTGCCCAAAC | TTCACAGCAT | TAGGGACAGG | 780 |
| AATGGAACAC | ACTTGGATGC | AGGGGCTTTG | ACCACGACCT | TTGAAGAGCT | TCATTTTGAG | 840 |
| ATCAAGCCCC | ACGATGACTG | CACAGTAGAG | CAAATCTATG | AGATTTTGAA | AATCTACCAA | 900 |
| CTCATGGACC | ACAGTAACAT | GGACTGCTTC | ATCTGCTGTA | TCCTCTCCCA | TGGAGACAAG | 960 |
| GGCATCATCT | ATGGCACTGA | TGGACAGGAG | CCCCCCATCT | ATGAGCTGAC | ATCTCAGTTC | 1020 |
| ACTGGTTTGA | AGTGCCCTTC | CCTTGCTGGA | AAACCCAAAG | TGTTTTTTAT | TCAGGCTTGT | 1080 |
| CAGGGGGATA | ACTACCAGAA | AGGTATACCT | GTTGAGACTG | ATTCAGAGGA | GCAACCCTAT | 1140 |
| TTAGAAATGG | ATTTATCATC | ACCTCAAACG | AGATATATCC | CGGATGAGGC | TGACTTTCTG | 1200 |
| CTGGGGATGG | CCACTGTGAA | TAACTGTGTT | TCCTACCGAA | ACCCTGCAGA | GGGAACCTGG | 1260 |
| TACATCCAGT | CACTTTGCCA | GAGCCTGAGA | GAGCGATGTC | CTCGAGGCGA | TGATATTCTC | 1320 |
| ACCATCCTGA | CTGAAGTGAA | CTATGAAGTA | AGCAACAAGG | ATGACAAGAA | AAACATGGGG | 1380 |
| AAACAGATGC | CTCAGCCTAC | TTTCACACTA | AGAAAAAAAC | TTGTCTTCCC | TTCTGATTGA | 1440 |

(2) INFORMATION FOR SEQ ID NO:12:

(i) SEQUENCE CHARACTERISTICS:
  (A) LENGTH: 479 amino acids
  (B) TYPE: amino acid
  (D) TOPOLOGY: linear (ii) MOLECULE TYPE: protein (xi) SEQUENCE DESCRIPTION: SEQ ID NO:12:

```
Met Asp Phe Ser Arg Asn Leu Tyr Asp Ile Gly Glu Gln Leu Asp Ser
 1               5                  10                  15

Glu Asp Leu Ala Ser Leu Lys Phe Leu Ser Leu Asp Tyr Ile Pro Gln
                20                  25                  30

Arg Lys Gln Glu Pro Ile Lys Asp Ala Leu Met Leu Phe Gln Arg Leu
            35                  40                  45

Gln Glu Lys Arg Met Leu Glu Glu Ser Asn Leu Ser Phe Leu Lys Glu
        50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
                100                 105                 110

Ser Arg Ser Glu Leu Arg Ser Phe Lys Phe Leu Leu Gln Glu Glu Ile
            115                 120                 125

Ser Lys Cys Lys Leu Asp Asp Asp Met Asn Leu Leu Asp Ile Phe Ile
        130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
                180                 185                 190

Pro Asp Glu Phe Ser Asn Gly Glu Glu Leu Cys Gly Val Met Thr Ile
            195                 200                 205

Ser Asp Ser Pro Arg Glu Gln Asp Ser Glu Ser Gln Thr Leu Asp Lys
        210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
                260                 265                 270

Thr Phe Glu Glu Leu His Phe Glu Ile Lys Pro His Asp Asp Cys Thr
            275                 280                 285

Val Glu Gln Ile Tyr Glu Ile Leu Lys Ile Tyr Gln Leu Met Asp His
        290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Pro Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
        355                 360                 365

Ile Pro Val Glu Thr Asp Ser Glu Glu Gln Pro Tyr Leu Glu Met Asp
```

-continued

| | | | | | 370 | | | | | 375 | | | | | 380 | | | |
|---|---|---|---|---|---|---|---|---|---|---|---|---|---|---|---|---|---|---|
| Leu 385 | Ser | Ser | Pro | Gln | Thr 390 | Arg | Tyr | Ile | Pro | Asp 395 | Glu | Ala | Asp | Phe | Leu 400 |
| Leu | Gly | Met | Ala | Thr 405 | Val | Asn | Asn | Cys | Val 410 | Ser | Tyr | Arg | Asn | Pro 415 | Ala |
| Glu | Gly | Thr | Trp 420 | Tyr | Ile | Gln | Ser | Leu 425 | Cys | Gln | Ser | Leu | Arg 430 | Glu | Arg |
| Cys | Pro | Arg 435 | Gly | Asp | Asp | Ile | Leu 440 | Thr | Ile | Leu | Thr | Glu 445 | Val | Asn | Tyr |
| Glu | Val 450 | Ser | Asn | Lys | Asp | Asp 455 | Lys | Lys | Asn | Met | Gly 460 | Lys | Gln | Met | Pro |
| Gln 465 | Pro | Thr | Phe | Thr | Leu 470 | Arg | Lys | Lys | Leu | Val 475 | Phe | Pro | Ser | Asp | |

NUCLEIC ACIDS MOLECULES ENCODING CASPASE-8H AND CASPASE-8I

The invention relates to the field of programmed cell death.

BACKGROUND OF THE INVENTION

In multicellular organisms, homeostasis is maintained by balancing the rate of cell proliferation against the rate of cell death. Cell proliferation is influenced by numerous growth factors and the expression of proto-oncogenes, which typically encourage progression through the cell cycle. In contrast, numerous events, including the expression of tumor suppressor genes, can lead to an arrest of cellular proliferation.

In differentiated cells, a particular form of cell death called apoptosis is carried out when an internal suicide program is activated. This program can be initiated by a variety of external signals as well as signals that are generated within the cell in response to, for example, genetic damage. For many years, the magnitude of apoptotic cell death was not appreciated because the dying cells are quickly eliminated by phagocytes, without an inflammatory response.

The mechanisms that mediate apoptosis have been intensively studied. These mechanisms involve the activation of endogenous proteases, loss of mitochondrial function, and structural changes such as disruption of the cytoskeleton, cell shrinkage, membrane blebbing, and nuclear condensation due to degradation of DNA. The various signals that trigger apoptosis are thought to bring about these events by converging on a common cell death pathway that is regulated by the expression of genes that are highly conserved from worms, such as C. elegans, to humans. In fact, invertebrate model systems have been invaluable tools in identifying and characterizing the genes that control apoptosis. Through the study of invertebrates and more evolved animals, numerous genes that are associated with cell death have been identified, but the way in which their products interact to execute the apoptotic program is poorly understood.

Recently, several polypeptides were discovered which form a complex that transmits an apoptotic signal when the Fas/APO-1 receptor is bound (Boldin et al., Cell 85:803, 1996; Muzio et al., Cell 85:817, 1996). This receptor, also known as CD95, is present on the surface of a wide variety of cells (Boldin et al., supra; Muzio et al., supra). The Fas/APO-1 receptor and the TNF receptor (described below) are classified as members of the TNF/nerve growth factor receptor family and both share a region of homology designated the "death domain" (Boldin et al., supra; Muzio et al., supra). The death domain of the Fas/APO1 receptor interacts with FADD (Fas-associating protein with death domain, also known as MORT1) and RIP (receptor interacting protein), forming a complex that, when joined by Caspase-8, constitutes the Fas/APO-1 death-inducing signalling complex (Boldin et al., supra; Muzio et al., supra). The interaction between Fas/APO-1 and FADD is mediated by their respective C-terminal death domains (Chinnaiyan et al., Cell 81:505–512, 1995). Caspase-8 contains two N-terminal stretches of approximately 60 amino acids that are homologous to the DED of FADD (Muzio et al., supra). The remainder of Caspase-8 is highly homologous to the ICE/CED-3 family of cysteine proteases, which induce cell death if overexpressed. A number of forms of Caspase-8 have been described (Boldin et al., supra).

Caspase-8 may also be an important part of a second complex which is involved in cell death. This complex forms in association with the intracellular portion of the tumor necrosis factor (TNF) receptor (TNFR-1 or p55-R), and includes Caspase-8, TRADD (TNFR-1-associated death domain protein), and FADD/MORT1 (Boldin et al., supra; Muzio et al., supra).

SUMMARY OF THE INVENTION

The present invention relates to the discovery and characterization of two novel forms of Caspase-8. The first Caspase-8 of the invention, Caspase-8h, encodes a 220 amino acid polypeptide which includes two FADD death effector domains. The second caspase of the invention, Caspase-8i, encodes an 81 amino acid polypeptide having one FADD death effector domain.

The invention encompasses nucleic acid molecules encoding Caspase-8h and Caspase-8i, vectors containing these nucleic acid molecules, cells harboring recombined DNA encoding Caspase-8h and/or Caspase-8i, host fusion proteins which include Caspase-8h and/or Caspase-8i, transgenic animals which express Caspase-8h and/or Caspase-8i, recombinant knock-out animals which fail to express Caspase-8.

By "isolated nucleic acid molecule" is meant a nucleic acid molecule that is separated from either the 5' or the 3' coding sequence with which it is immediately contiguous in the naturally occurring genome of an organism. An isolated nucleic acid molecule is also referred to as "recombinant nucleic acid molecule".

The nucleic acid molecules of the invention can be inserted into transcription and/or translation vectors, as described below, which will facilitate expression of the insert. The nucleic acid molecules and the polypeptides they encode can be used directly as diagnostic or therapeutic agents, or (in the case of a polypeptide) can be used to generate antibodies that, in turn, are therapeutically useful. Accordingly, expression vectors containing the nucleic acid of the invention, cells transfected with these vectors, the polypeptides expressed, and antibodies generated, against either the entire polypeptide or an antigenic fragment thereof, are among the preferred embodiments.

As used herein, the term "transfected cell" means any cell into which (or into an ancestor of which) has been introduced, by means of recombinant DNA techniques, a nucleic acid encoding a polypeptide of the invention (e.g., a Caspase-8h polypeptide or a Caspase-8i polypeptide).

As used herein, both "protein" and "polypeptide" mean any chain of amino acid residues, regardless of length or post-translational modification (e.g., glycosylation or phosphorylation). The polypeptides of the invention are referred to as "substantially pure," meaning that they are at least 60% by weight (dry weight) the polypeptide of interest, e.g., a Caspase-8 polypeptide or a Caspase-8i polypeptide. Preferably, the polypeptide is at least 75%, more preferably at least 90%, and most preferably at least 99%, by weight, the polypeptide of interest. Purity can be measured by any appropriate standard method, e.g., column chromatography, polyacrylamide gel electrophoresis, or HPLC analysis. The polypeptide can be a naturally occurring, synthetic, or a recombinant molecule consisting of a hybrid with one portion, for example, being encoded by all or part of the Caspase-8h or Caspase-8i gene, and a second portion being encoded by all or part of a second gene. For example, the AZB polypeptide may be fused to a hexa-histidine tag to facilitate purification of bacterially expressed protein, or to a hemagglutinin tag to facilitate purification of protein expressed in eukaryotic cells.

The polypeptides of the invention can also be chemically synthesized, or they can be purified from tissues in which they are naturally expressed, according to standard biochemical methods of purification.

Also included in the invention are "functional polypeptides," which possess one or more of the biological functions or activities of the caspase-8h or caspase-8i. These functions or activities are described in detail below and concern, primarily, inhibition of apoptosis and/or the ability to bind some or all of the proteins which normally bind to caspase-8h or caspase-8i. A functional polypeptide is also considered within the scope of the invention if it serves as an immunogen for production of antibodies that specifically bind to caspase-8h or caspase-8i. In many cases, functional polypeptides retain one or more domains present in the naturally-occurring form of the polypeptide. For example, a functional polypeptide may posses one or more FADD death effector domains. It is well within the abilities of skilled artisans to determine whether a polypeptide, regardless of size, retains the function activity of a polypeptide of the invention.

The functional polypeptides may contain a primary amino acid sequence that has been modified from those disclosed herein. Preferably these modifications consist of conservative amino acid substitutions, as described herein.

The members of a pair of molecules (for example, an antibody-antigen pair) are said to "specifically bind" to each other if they bind to each other with greater affinity than to other molecules, even those that are structurally or functionally related to a member of the specific binding pair.

The invention also encompasses compounds which modulate the expression or activity of Caspase-8h and/or Caspase-8i, including small molecules (i.e., molecules with a molecular weight below about 500), large molecules (i.e., molecules with a molecular weight above about 500), and nucleic acid molecules that can be used to inhibit the expression of these genes (for example, antisense and ribozyme molecules) or to enhance their expression (for example, expression constructs that place nucleic acid sequences encoding either caspase-8h or caspase-8i under the control of a strong promoter system), and transgenic animals that express a caspase-8h or caspase-8i transgene. Because caspase-8 gene encodes a number of alternatively spliced forms of caspase-8, the level of caspase-8h or caspase-8i expression can be altered by altering the splicing pattern of the caspase-8 primary RNA transcript.

Caspase-8h and/or Caspase-8i function can be altered either by altering the expression of Caspase-8h and/or Caspase-8i (i.e., altering the amount of Caspase-8h and/or Caspase-8i present in a given cell) or by altering the activity of Caspase-8h and/or Caspase-8i (i.e., altering a Caspase-8h and/or Caspase-8i function, e.g., binding to Fas/APO-1 receptor complex).

The invention encompasses methods of treatment including a method of treating a patient who is suffering from a disorder associated with an abnormal rate of apoptotic cell death, abnormal activity of the Fas/APO-1 receptor complex, or abnormal activity of the TNF receptor complex by administering a compound that modulates the expression of Caspase-8h and/or Caspase-8i (at the DNA, mRNA or protein level, e.g., by altering mRNA splicing) or by altering the activity of Caspase-8h and/or Caspase-8i. Examples of such compounds include small molecules, antisense nucleic acid molecules, and ribozymes. Because Caspase-8h and Caspase-8i lack the ICE/CED-3 domain that is required for carrying out apoptosis, but have FADD death effector domains required for interaction with Fas/APO-1, they may compete with other forms of Caspase-8 for binding to the Fas/APO-1 complex. Accordingly, increased expression of Caspase-8h and/or Caspase08i may decrease Fas/APO-1 mediated apoptosis (or TNF receptor mediated apoptosis). A patient who is suffering from an abnormally high rate of apoptotic cell death may be treated by the administration of a ligand (for example, a synthetic ligand) that mediates oligomerization between the Fas/APO-1 receptor complex or the TNF receptor complex and Caspase-8h or Caspase-8i, increases the expression of Caspase-8h or Caspase-8i, or increases the activity of Caspase-8h or Caspase-8i. Accordingly, the invention features therapeutic compositions that contain the compounds or ligands described above.

A patient who is suffering from a disorder associated with excessive apoptotic cell death, abnormal activity of the Fas/APO-1 receptor complex, or abnormal activity of the TNF receptor complex can be treated by the administration of an expression vector that contains a nucleic acid molecule encoding Caspase-8h or Caspase-8i by administering the polypeptide directly to the patient's cells (either in vivo or ex vivo). These methods are described more fully below.

Certain disorders are associated with an increased number of surviving cells, which are produced and continue to survive or proliferate when apoptosis is inhibited. These disorders include cancer (particularly follicular lymphomas, carcinomas associated with mutations in p53, and hormone-dependent tumors such as breast cancer, prostate cancer, and ovarian cancer), autoimmune disorders (such as systemic lupus erythematosis, immune-mediated glomerulonephritis), and viral infections (such as those caused by herpesviruses, poxviruses, and adenoviruses).

Failure to remove autoimmune cells that arise during development or that develop as a result of somatic mutation during an immune response can result in autoimmune disease. One of the molecules that plays a critical role in regulating cell death in lymphocytes is the cell surface receptor for Fas.

Populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis.

A wide variety of neurological diseases are characterized by the gradual loss of specific sets of neurons. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death.

In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses.

Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

In addition, the present invention encompasses methods and compositions for the diagnostic evaluation, typing, and prognosis of disorders associated with apoptotic cell death. The disorder can be associated with either an increase or a decrease in the incidence of apoptotic cell death. For example, the nucleic acid molecules of the invention can be used as diagnostic hybridization probes to detect, for example, expression of Caspase-8h or Caspase-8i. Such methods may be used to classify cells by the level of Caspase-8h or Caspase-8i expression. For example higher Caspase-8h or Caspase-8i expression may be associated with a lower rate of apoptosis.

Alternatively, the nucleic acid molecules can be used as primers for diagnostic PCR analysis for the identification of gene mutations, allelic variations and splice regulation defects in the caspase-8 gene. The present invention further provides for diagnostic kits for the practice of such methods.

In particular, the invention described below encompasses Caspase-8h and Caspase-8i, polypeptides corresponding to functional domains of Caspase-8h or Caspase-8i (e.g., the "DED" domain), mutated, truncated, or deleted polypeptides that retain the functional activity of Caspase-8h and Caspase-8i (for example, a polypeptide in which one or more amino acid residues have been substituted or deleted from the death effector domain), and fusion proteins (as described below).

Polypeptides that exhibit at least 70%, preferably at least 80%, more preferably 90%, and most preferably 95% of the activity of the Caspase-8h and Caspase-8i polypeptides described herein are considered within the scope of the invention.

The invention encompasses nucleic acids and polypeptides that have a sequence that is substantially identical to a Caspase-8h or Caspase-8i nucleic acid or polypeptide. The term "substantially identical" is hereby defined as a polypeptide or nucleic acid having a sequence has at least 90%, preferably 95%, and more preferably 98% or 99% or more identity to the sequence of a reference amino acid or nucleic acid sequence. For polypeptides, the length of the reference polypeptide sequence will generally be at least 16 amino acids, at least 20 amino acids, at least 25 amino acids, or preferably 35 amino acids. For nucleic acids, the length of the reference nucleic acid sequence will generally be at least 50 nucleotides, at least 60 nucleotides, at least 75 nucleotides, and or at least 110 nucleotides.

Sequence identity can be measured using sequence analysis software (e.g., Sequence Analysis Software Package of the Genetics Computer Group, University of Wisconsin Biotechnology Center, 1710 University Avenue, Madison, Wis. 53705) with the default parameters specified therein.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference polypeptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria.

The reference nucleic acid or polypeptide can be a naturally-occurring molecule, for example, a Caspase-8h encoding nucleic acid molecule, a Caspase-8i encoding nucleic acid molecule, a Caspase-8h polypeptide, or a Caspase-8i polypeptide.

By "transgenic animal" is meant any animal containing cells that bear genetic information received, directly or indirectly, by deliberate genetic manipulation at the subcellular level, such as DNA received by microinjection or by infection with recombinant virus. Thus, animals of the invention are those with one or more cells that contain a recombinant DNA molecule of the invention and, in this context, the term "animal" denotes all animals except *Homo sapiens*. Farm animals (pigs, goats, sheep, cows, horses, rabbits, and the like), rodents (such as rats, guinea pigs, and mice), non-human primates (for example, baboons, monkeys, and chimpanzees), and domestic animals (for example, dogs and cats) are especially preferred.

It is also preferred that the nucleic acid molecule becomes integrated with the animal's chromosomes, but the use of DNA sequences that replicate extrachromosomally, such as might be engineered into yeast artificial chromosomes, is also contemplated.

The term "transgenic animal" also includes animals in which the genetic information has been taken up and integrated into a germ line cell. These animals typically have the ability to transfer the genetic information to their offspring. If the offspring in fact possess some or all of the genetic information delivered to the parent animal, then they, too, are transgenic animals.

In another embodiment, the invention features methods of identifying compounds that modulates apoptotic cell death by modulating the expression or activity of Caspase-8h and/or Caspase-8i by assessing the expression or activity of Caspase-8h and/or Caspase-8i in the presence and absence of said compound. A difference in the level of expression or activity in the presence of the compound (compared with the level of expression or activity in the absence of the compound) indicates that the compound is capable of modulating apoptotic cell death by modulating the expression of Caspase-8h and/or Caspase-8i. Expression can be assessed either at the level of gene expression (e.g., by measuring mRNA) or protein expression by techniques that are well known to skilled artisans. The activity of Caspase-8h and/or Caspase-8i can be assessed functionally, i.e., by assaying the ability of the compound to inhibit apoptosis following activation of the Fas/APO-1 or TNF receptor complexes.

The invention features an isolated nucleic acid molecule comprising a nucleotide sequence encoding a polypeptide that is at least 85% identical to SEQ ID NO:2; and an isolated nucleic acid molecule comprising a nucleotide sequence encoding a polypeptide that is at least 85% identical to SEQ ID NO:4. In one embodiment, the molecule encodes a polypeptide capable of selectively binding to the death effector domain of FADD.

In other aspects the invention features: an isolated nucleic molecule encoding the amino acid sequence of SEQ ID NO:2, an isolated nucleic acid molecule which includes the nucleotide sequence of SEQ ID NO:3, an isolated nucleic acid molecule of claim which encodes the amino acid sequence of SEQ ID NO:4, and isolated molecule of which includes the nucleotide sequence of SEQ ID NO:2, an isolated nucleic acid molecule which includes the molecule of ATCC 97877, and an isolated nucleic acid molecule which includes the molecule of ATCC 97878.

In another aspect the invention features a vector which includes an above-described nucleic acid molecule. In various specific embodiments, the vector is an expression vector, includes a regulatory element, includes a regulatory element selected from the group consisting of the cytomegalovirus hCMV immediate early gene, the early promoter of SV40 adenovirus, the late promoter of SV40 adenovirus, the lac system, the trp system, the TAC system, the TRC system, the major operator and promoter regions of phage λ, the control regions of fd coat protein, the promoter for 3-phosphoglycerate kinase, the promoters of acid phosphatase, and the promoters of the yeast α-mating factors, includes a regulatory element that directs tissue-specific expression, includes a reporter gene, includes a reporter gene is selected from the group consisting of β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT), is a plasmid, is a virus, and is a retrovirus.

In another aspect, the invention features a genetically engineered host cell, particularly a eukaryotic cell, which includes an expression vector described above.

In other aspects, the invention features a substantially pure polypeptide having the amino acid sequence encoded by an above-described nucleic acid molecule. The invention also features a polypeptide which includes a heterologous polypeptide other than a Caspase-8 polypeptide.

In other aspects the invention features an antibody that binds Caspase-8h and an antibody that binds Caspase-8i.

In yet another aspect the invention features a transgenic animal harboring a nucleic acid molecule described above.

The invention also features a method for determining whether a patient is suffering from a disorder associated with an abnormal rate of apoptotic cell death, the method includes obtaining a biological sample (e.g., a tumor sample) from the patient and quantitating the level of caspase-8h expression in the biological sample. In related methods the method includes quantitating mRNA encoding Caspase-8h or quantitating Caspase-8h protein.

The invention also features a method for determining whether a patient is suffering from a disorder associated with an abnormal rate of apoptotic cell death, the method includes obtaining a biological sample (e.g., a tumor sample) from the patient and quantitating the level of caspase-8i expression in the biological sample. In related methods the method includes quantitating mRNA encoding Caspase-8i or quantitating Caspase-8i protein.

Related methods entail an RNase protection assay, Northern blot analysis, amplification by RT-PCR, or Western blot analysis.

The invention also features a method of treating a patient who is suffering from a disorder associated with abnormal activity of the Fas/APO-1 receptor complex, the method includes administering to the patient a compound that modulates the expression or activity of Caspase-8h. In related methods the compound includes a small molecule, an antisense nucleic acid molecule, or a ribozyme.

The invention also includes a method of treating a patient who is suffering from a disorder associated with an abnormal activity of the TNF receptor complex, the method includes administering to the patient a compound that modulates the expression or activity of Caspase-8i. In related methods the compound includes a small molecule, an antisense nucleic acid molecule, or a ribozyme.

The invention also features therapeutic compositions which include the compounds of the above-described treatment methods.

In another aspect the invention features a method for treating a patient who is suffering from a disorder associated with abnormal activity of the Fas/APO-1 receptor complex, the method includes administering a compound that mediates oligomerization between the Fas/APO-1 receptor complex and Caspase-8h or Caspase-8i.

The methods of the invention include a method for treating a patient who is suffering from a disorder associated with abnormal activity if the TNF receptor complex, the method includes administering a compound that mediates oligomerization between the TNF receptor complex and Caspase-8h or Caspase-8i.

In related methods the patient is suffering from acquired immune deficiency syndrome (AIDS), a neurodegenerative disorder, a myelodysplastic syndrome, an ischemic injury, or a toxin-induced injury. In other related methods, the compound is synthetic.

The invention also features, a method of treating a patient who is suffering from a disorder associated with excessive apoptotic cell death, the method including administering to the patient a caspase-8h or caspase-8i nucleic acid molecule, and a method of treating a patient who is suffering from a disorder associated with excessive apoptotic cell death, the method including administering to the patient a Caspase-8h polypeptide or a Caspase-8i polypeptide.

In another aspect the invention features a of identifying a compound that modulates expression of Caspase-8h, the method includes assessing the expression of Caspase-8h in the presence and absence of the compound.

In yet another aspect the invention features a method of identifying a compound that modulates expression of Caspase-8i, the method includes assessing the expression of Caspase-8i in the presence and absence of the compound.

The invention features a method for treating a patient who is suffering from an abnormally low rate of apoptotic cell death, the method including administering a compound that mediates oligomerization between the Fas/APO-1 receptor complex and Caspase-8h or Caspase-8i; and a method for treating a patient who is suffering from an abnormally low rate of apoptotic cell death, the method including administering a compound that mediates oligomerization between the TNF receptor complex and Caspase-8h or Caspase-8i.

The invention also features a method of identifying a compound that modulates the activity of Caspase-8h, the method including assessing the activity of Caspase-8h in the presence and absence of the compound; and a method of identifying a compound that modulates the activity of Caspase-8i, the method including assessing the activity of Caspase-8i in the presence and absence of the compound.

In other aspects the invention includes a method for determining whether a selected compound modulates oligomerization between the Fas/APO-1 receptor complex and Caspase-8h or Caspase-8i, the method including measuring oligomerization of the Fas/APO-1 receptor complex and Caspase-8h or Caspase-8i in the presence and absence of the selected compound; and a method for determining whether a selected compound modulates oligomerization between the TNF receptor complex and Caspase-8h or Caspase-8i, the method including measuring oligomerization of the TNF receptor complex and Caspase-8h or Caspase-8i in the presence and absence of the selected compound.

The invention features an isolated nucleic acid molecule which hybridizes under stringent conditions to a nucleic acid molecule having the nucleotide sequence of SEQ ID NO:1, the isolated nucleic acid molecule encoding Caspase-8h; an isolated nucleic acid molecule which hybridizes under stringent conditions to a nucleic acid molecule having the nucleotide sequence of SEQ ID NO:3, the isolated nucleic acid molecule encoding Caspase-8i; an isolated nucleic acid molecule includes a nucleotide sequence which is at least 90% identical to the nucleotide sequence of SEQ ID NO:1, the isolated nucleic acid molecule encoding Caspase-8h; and an isolated nucleic acid molecule includes a nucleotide sequence which is at least 90% identical to the nucleotide sequence of SEQ ID NO:3, the isolated nucleic acid molecule encoding Caspase-8i.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the detailed description and from the claims. Although materials and methods similar or equivalent to those described herein can be used in the practice or testing of the invention, the preferred materials and methods are described below.

BRIEF DESCRIPTION OF THE DRAWINGS

FIG. 2 is a representation of the nucleic acid sequence of caspase-8h (SEQ ID NO:1).

FIG. 3 is a representation of the amino acid sequence of Caspase-8h (SEQ ID NO:2).

FIG. 4 is a representation of the nucleic acid sequence of caspase-8i (SEQ ID NO:3).

FIG. 5 is a representation of the amino acid sequence of Caspase-8i (SEQ ID NO:4).

FIG. 6 is a representation of the nucleic acid sequence of caspase-8 (SEQ ID NO:11).

FIG. 7 is a representation of the amino acid sequence of Caspase-8 (SEQ ID NO:12).

DETAILED DESCRIPTION

Figure 1:
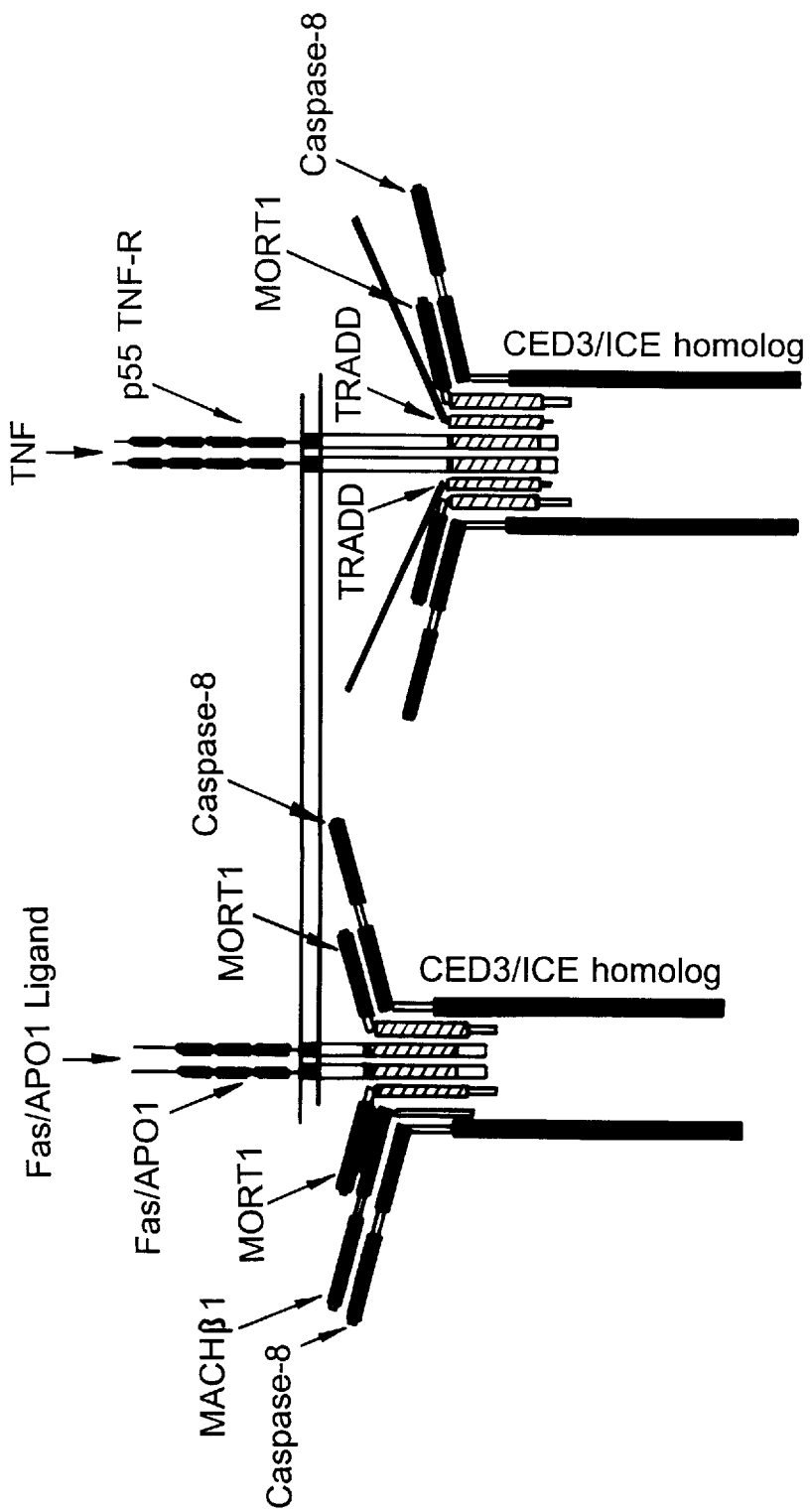
FIG. 1 is a schematic diagram illustrating the proteins that interact with the Fas/APO-1 (left hand side) and p55 (right hand side) receptors and thereby participate in the induction of cell death.
Figure 8:
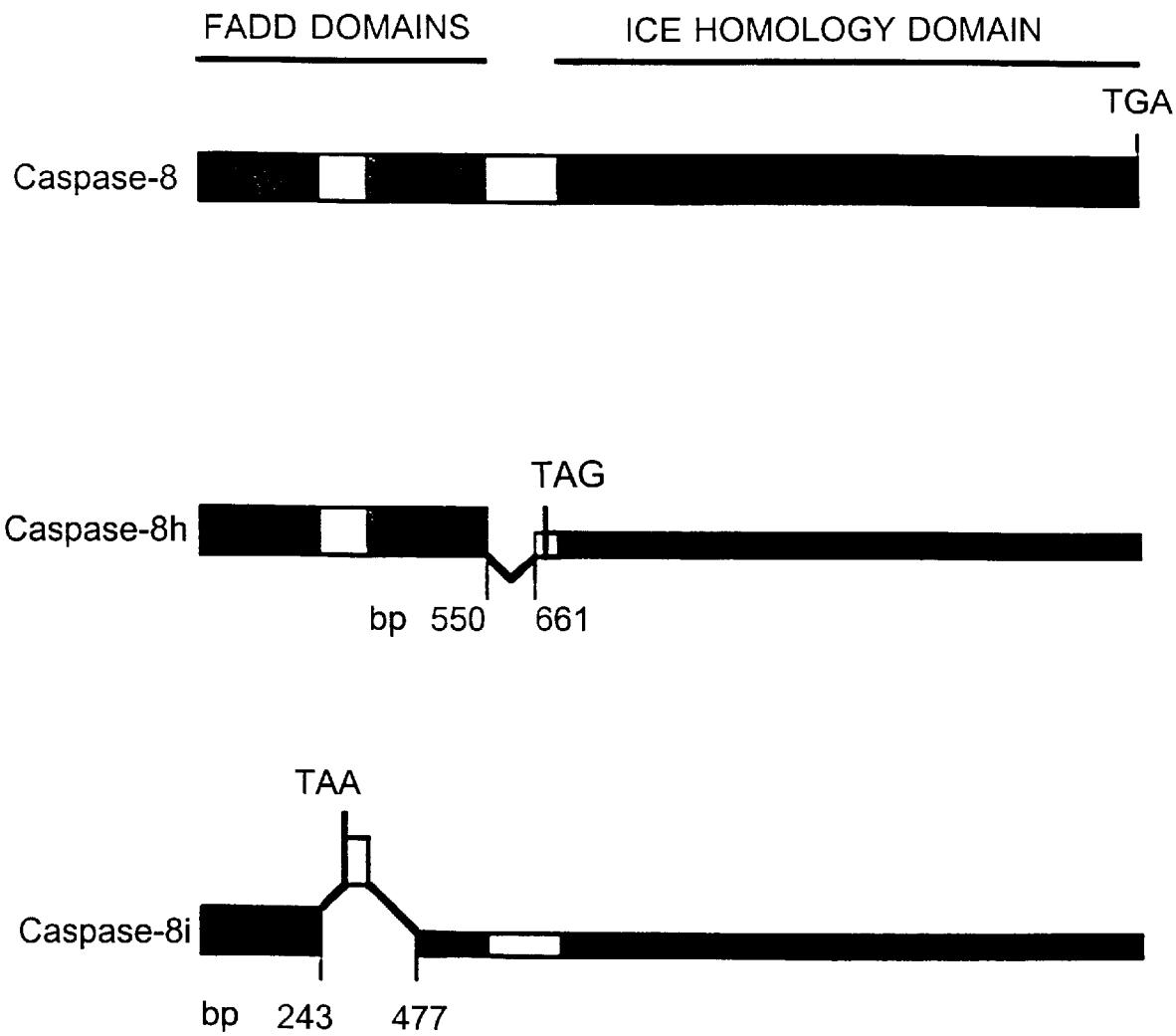
FIG. 8 is a schematic representation of Caspase-8 pre-mRNA, Caspase-8h mRNA (showing the location of the TAG stop codon), and Caspase-8i mRNA (showing the location of the TAA stop codon).

The present invention relates to the discovery, identification, and characterization of two nucleic acid molecules that encode novel Caspase-8 polypeptides, i.e., Caspase-8h and Caspase-8i. These caspase molecules are involved in signal transduction triggered by the activation of the Fas/APO1 (CD95) or p55 (TNFR1) receptors by virtue of their ability to bind FADD/MORT1 within the receptor complex. They lack, however, the ICE/CED-3 cysteine protease domain present in some forms of Caspase-8. Therefore caspase-8h and caspase-8i do not transmit the signal generated by receptor binding, as the full-length Caspase-8 protein would.

Identification and Characterization of Nucleic Acid Molecules Encoding Caspase-8h and Caspase-8i Standard techniques were used to generate cDNA from human placental mRNA, and the polymerase chain reaction (PCR) was performed to selectively amplify a portion of that cDNA. The reaction included two oligonucleotide primers that were based on the sequence of caspase-8: 5'-ATGGACTTCAGCAGAAATCTTTATG-3' (SEQ ID NO:5) and 5'-TCAATCAGAAGGGAAGACAAGTTTT-3' (SEQ ID NO:6). The amplified cDNA fragment was subcloned into the plasmid vector pCR2.1 (InVitrogen, San Diego, Calif.), and four independent clones were prepared. When these clones were analyzed by digestion with EcoRI, three different restriction maps were seen. Sequence analysis confirmed that three of the four clones were distinct and that they represented different forms of the caspase-8 gene. One of the clone represented the presumptively full-length caspase-8 cDNA, as described by Muzio et al. (*Cell* 85:817–827, 1996) and Boldin et al. (Cell 85:803–815, 1996). The other two clones contained cDNA encoding novel forms of Caspase-8 that lack the ICE/CED-3 cysteine protease domain present in full-length Caspase-8. According to the convention recently proposed (*Cell* 87:171, 1996), these forms have been named Caspase-8h and Caspase-8i.

Caspase-8h is predicted to encode a polypeptide that is 220 amino acids in length and that contains two tandem domains that are similar to the FADD death effector domain (DED; see below). Caspase-8i is predicted to encode a much shorter polypeptide, of 81 amino acid residues, that consists of only the first FADD DED-like domain.

Caspase-8 is believed to mediate the apoptotic signal that is generated when the Fas/APO-1 (CD95) receptor is bound by its natural ligand or specific agonist antibody (Baglioni, In "Tumor Necrosis Factors: The Molecules and Their Emerging Role in Medicine," B. Beutler, Ed., Raven Press, New York, N.Y., pp. 425–438, 1992; Itoh et al., *J. Biol. Chem.* 268:10932–10937, 1993). It is thought that Caspase-8 also mediates the apoptotic signal that is generated when the TNF receptor (TNFR-1 or p55-R) is bound by its natural ligand or specific agonist antibody. Both of these receptors are members of the tumor necrosis factor (TNF)/ nerve growth factor receptor family, which also includes TNFR-2, low affinity NGFR, CD40, CD30, and others (Smith et al., *Science* 248:1019–1023, 1990).

While the members of this receptor family are characterized by the presence of cysteine-rich repeats in their extracellular domains, Fas/APO-1 and TNFR-1 also share a region of homology that is designated the "death domain" because it is required to signal apoptosis (Itoh and Nagata, J. Biol. Chem. 268:10932–10937, 1993). This shared death domain suggests that both receptors interact with a related set of signal-transducing molecules.

Three of these signal-transducing molecules were recently discovered: TRADD (TNFR-1-associated death domain), FADD/MORT1 (Fas-associating protein with death domain), and RIP (receptor-interacting protein) (Chinnaiyan et al. Cell 81:505–512, 1995; Stanger et al., Cell 81:513–523, 1995; Hsu et al., Cell 81:495–504, 1995; Cleveland and Ihle, Cell 81:479–482, 1995). The way in which these proteins are believed to interact with the Fas/APO1 and TNF receptors is illustrated in FIG. 1. A dominant negative version of FADD (FADD-DN) blocks both TNF-induced and CD95-induced apoptosis, suggesting that FADD functions as the common signaling conduit for cytokine-mediated cell death (Chinnaiyan et al. J. Biol. Chem. 271:4961–4965, 1996; Hsu et al. Cell 84:299–308, 1996).

In addition, a protein that binds FADD/MORT1 has been discovered. This protein was named FLICE by one group of investigators (Muzio et al., supra.) and MACH by a second group that published their discovery at the same time (Boldin et al. Cell 85:803–815, 1996). According to recently adopted nomenclature, (Cell 87:171, 1996) this protein is now called Caspase-8.

The recruitment of Caspase-8 to the receptor complex (via FADD/MORT1) results in activation of the protease activity of Caspase-8, which is required for apoptosis. Accordingly, the novel forms of Caspase-8 described herein (Caspase-8h and Caspase-8i), which lack this domain but retain the ability to bind FADD/MORT1 (via their FADD death effector domains), would effectively compete with full length Caspase-8 for binding to FADD/MORT1 and thereby prevent the cell from undergoing apoptosis.

Caspase-8h and Caspase-8i Contain One or Two Domains that are Homologous to the Death Effector Domain of FADD The 117 N-terminal amino acids of FADD/MORT1 are capable of triggering apoptosis. Thus, this segment contains the death effector domain (DED) referred to above and shown as striped segments in FIG. 1 (see also Chinnaiyan et al., supra). Muzio et al. (supra) reported that Caspase-8 (then called FLICE) contains two N-terminal stretches of approximately 60 amino acids that are homologous to the DED of FADD; a search revealed that residues 7–75 and 101–169 of Caspase-8 "matched" the DED of FADD (residues 4–76), sharing 39% identity (55% similarity) and 28% identity (55% similarity), respectively (Muzio et al., supra) . The remainder of the Caspase-8 protein is highly homologous to the ICE/CED-3 family, particularly in the regions corresponding to the active subunits of ICE (Muzio et al., supra).

Tissue Distribution of Caspase-8

Caspase-8 is constitutively expressed in many fetal and adult human tissues (including colon, small intestine, ovary, thymus, spleen, kidney, liver, and lung), but not in the fetal brain (Muzio et al., supra). There was a relative increase in the expression of caspase-8 in peripheral blood leukocytes, which was reported to be consistent with the important role of FAS/APO1-signaling (CD95-signaling) in lymphocyte homeostasis (Nagata and Golstein, Science 267:1449–1456, 1995).

An Assay for FAS/APO-1 Mediated Apoptosis

An assay for Fas/APO-1 mediated apoptosis can be used in screening assays to identify compounds that increase or decrease apoptosis. The compounds identified using these assays may alter in the level of apoptosis, the activity of the Fas/APO-1 receptor complex, or the activity of the TNF receptor complex by modulating the expression or activity of Caspase-8h or Caspase-8i. Compounds identified in these assays can be used as therapeutic compounds to treat disorders associated with an abnormal rate of apoptosis, abnormal activity of the Fas/APO-1 receptor complex, or abnormal activity of the TNF receptor complex.

Assays of Fas/APO-1 mediated apoptosis generally employ Fas/APO-1-expressing cells and an antibody directed against Fas/APO-1 which, upon binding to Fas/APO-1 receptor initiates apoptosis. The following assay is one example of such an assay.

MCF-7 breast carcinoma cells (approximately $2 \times 10^5$) are plated onto gridded 35 mm tissue culture dishes. Optionally, the cells can be transfected with DNA that directs the expression of a form of Caspase-8. For example, the cells an be transfected with 0.25 µg of CMVβ-gal and either: (1) 1 µg CMV-caspase-8, (2) CMV-caspase-8 and 4 µg CMV-caspase-8h, or (3) CMV-caspase-8i. The transfections are performed in the presence of 20 µl of lipofectin (Gibco/BRL) in 1 ml Optimem for six hours. Twenty-four hours after transfection, the cells are treated with anti-Fas antibody (CHII, Oncor, Gaithersburg, Md.) to induce apoptosis (the amount of antibody required is empirically determined). Forty-two hours after transfection, the cells are fixed with gluteraldehyde, and examined for β-galactosidase activity by staining with X-gal (according to standard and well known procedures). After staining, 200 successfully transfected cells per plate (as indicated by their blue color) are counted and scored as normal or apoptotic (apoptotic cells were small with conspicuous membrane blebbing). By transfecting cells with caspase-8, caspase-8h, or caspase-8i DNA one can examine the effect of the presence of the various forms of Caspase-8 on FAS/APO-1 mediated cell death. This assay allows one to identify compounds which increase or decrease apoptosis by carrying out the assay in the presence and absence of a selected compound and determining whether that compound increases or decreases apoptosis.

Other cell types, for example SHEP cells, can be used in the assay described above. Furthermore, the cells can be those of stably transfected cell lines.

Numerous substances, in addition to the anti-Fas antibody described above, are capable of inducing apoptosis in various cell types and can thus be used in assays of apoptosis. These substances include physiological activators, such as TNF family members, TGF-β, the neurotransmitters glutamate, dopamine, and NMDA (N-methyl-D-aspartate), calcium, and glucocorticoids. Cell death can also be induced when growth factors are withdrawn from the medium in which the cells are cultured. Additional inducers of apoptosis include heat shock, viral infection, bacterial toxins, expression of the oncogenes myc, rel, and E1A, expression of tumor suppressor genes, cytolytic T cells, oxidants, free radicals, gamma and ultraviolet irradiation, β-amyloid peptide, ethanol, and chemotherapeutic agents such as Cisplatin, doxorubicin, arabinoside, nitrogen mustard, methotrexate, and vincristine.

To assay cell death mediated by the TNF-receptor, a variation of the above-described assay can be used. In this variation, cell death is triggered by administering TNF in place of anti-Fas antibody. This assay can be used to identify compounds which increase or decrease apoptosis by simply carrying out the assay in the presence and absence of selected compounds.

Nucleic Acid Molecules of the Invention

Isolated nucleic acid molecules, as defined above, can be cDNA, genomic DNA, synthetic DNA, or RNA, and can be double-stranded or single-stranded (i.e., either a sense or an antisense strand). Fragments of these molecules, which are also considered within the scope of the invention, can be produced, for example, by the polymerase chain reaction (PCR) or generated by treatment with one or more restriction endonucleases. A ribonucleic acid (RNA) molecule can be produced by in vitro transcription.

The nucleic acid molecules of the invention can contain naturally occurring sequences, or sequences that differ from those that occur naturally, but, due to the degeneracy of the genetic code, encode the same polypeptide. In addition, these nucleic acid molecules are not limited to sequences that only encode functional polypeptides, and thus, can include some or all of the non-coding sequences that lie upstream or downstream from a coding sequence.

The nucleic acid molecules of the invention can be synthesized (for example, by phosphoramidite-based synthesis) or obtained from a biological cell, such as the cell of a mammal. Thus, the nucleic acids can be those of a human, mouse, rat, guinea pig, cow, sheep, horse, pig, rabbit, monkey, dog, or cat. Combinations or modifications of the nucleotides within these types of nucleic acids are also encompassed.

The isolated nucleic acid molecules of the invention encompass fragments that are not found as such in the natural state. Thus, the invention encompasses recombinant molecules, such as those in which a nucleic acid sequence (for example, a sequence encoding of Caspase-8h or Caspase-8i) is incorporated into a vector (for example, a plasmid or viral vector) or into the genome of a heterologous cell (or the genome of a homologous cell, at a position other than the natural chromosomal location). These circumstances are discussed further below.

In the event the nucleic acid molecules of the invention encode or act as antisense molecules, they can be used for example, to regulate transcription of the alternate forms of the invention. With respect to regulation of caspase-8h or caspase-8i transcription, such techniques can be used to diagnose and/or treat disorders associated with apoptotic cell death. These nucleic acids will be discussed further in that context.

In most cases, a DNA sequence encoding Caspase-8h or Caspase-8i will be one which produces Caspase-8h or Caspase-8i MRNA directly, without splicing. Thus, the DNA sequence will be based on the Caspase-8h or Caspase-8i mRNA sequence described herein rather than the caspase-8 genomic sequence.

In addition to the nucleotide sequences disclosed herein (see, for example SEQ ID NOS:1 and 3), equivalent forms may be present in other species, and can be identified and isolated by using the nucleotide sequences disclosed herein and standard molecular biological techniques. For example, homologs of caspase-8h or caspase-8i may be isolated from other organisms by performing PCR using two degenerate oligonucleotide primer pools designed on the basis of amino acid sequences of the alternatively spliced exons. Alternatively, the method used to identify human caspase-8h and caspase-8i can be used to isolate homologs from other species. The template for the reaction may be cDNA obtained by reverse transcription of mRNA prepared from, for example, human or non-human cell lines or tissues, particularly those known or suspected to express caspase-8. The PCR product may be subcloned and sequenced to ensure that the amplified nucleic acid sequence represents the sequence of caspase-8h or caspase-8i. Once identified, caspase-8h and caspase-8i in other species can be used, in turn, to develop animal models for the purpose of drug discovery. Alternatively, these forms of caspase-8 can be used in in vitro assays for the purpose of drug discovery.

The invention also encompasses nucleotide sequences that encode mutant Caspase-8h or Caspase-8i, or fragments thereof, that retain one or more functions of Caspase-8h or Caspase-8i, as described herein.

The invention also encompasses: (a) expression vectors that contain any of the foregoing Caspase-8h or Caspase-8i coding sequences and/or their complements (that is, "antisense" sequence); (b) expression vectors that contain Caspase-8h or Caspase-8i coding sequences operatively associated with a regulatory element that directs the expression of the coding sequences; (c) expression vectors containing caspase-8h or caspase-8i nucleic acid molecules and heterologous nucleic acid molecules, such as molecules encoding a reporter or marker; and (d) genetically engineered host cells that contain any of the foregoing expression vectors and thereby express the nucleic acid molecules of the invention in the host cell.

As used herein, regulatory elements include but are not limited to inducible and non-inducible promoters, enhancers, operators and other elements, which are known to those skilled in the art, that drive and regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences (for example, sequences that function as a marker or reporter) that can be used, for example, to produce a fusion protein (as described further below). Examples of marker or reporter genes include β-lactamase, chloramphenicol acetyltransferase (CAT), adenosine deaminase (ADA), aminoglycoside phosphotransferase ($neo^r$, $G418^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter.

The expression systems that may be used for purposes of the invention include but are not limited to microorganisms such as bacteria (for example, E. coli and B. subtilis) transformed with recombinant bacteriophage DNA, plasmid DNA or cosmid DNA expression vectors containing the nucleic acid molecules of the invention; yeast (for example, Saccharomyces and Pichia) transformed with recombinant yeast expression vectors containing the nucleic acid molecules of the invention (preferably containing the nucleic acid sequences of caspase-8h and/or caspase-8i); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing caspase-8h and/or caspase-8i nucleotide sequences; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter).

In bacterial systems, a number of expression vectors may be advantageously selected depending upon the use intended for the gene product being expressed. For example, when a large quantity of such a protein is to be produced, for the generation of pharmaceutical compositions of Caspase-8h or Caspase-8i polypeptides for raising antibodies to those proteins, vectors that are capable of directing the expression of high levels of fusion protein products that are readily purified may be desirable. Such vectors include, but are not limited to, the *E. coli* expression vector pUR278 (Ruther et al., *EMBO J.* 2:1791, 1983), in which the coding sequence of the insert may be ligated individually into the vector in frame with the lacZ coding region so that a fusion protein is produced; pIN vectors (Inouye and Inouye, *Nucleic Acids Res.* 13:3101–3109, 1985; Van Heeke and Schuster, *J. Biol. Chem.* 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. The coding sequence of the insert may be cloned individually into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (for example, see Smith et al. *J. Virol.* 46:584, 1983; Smith, U.S. Pat. No. 4,215,051).

In mammalian host cells, a number of viral-based expression systems may be utilized. In cases where an adenovirus is used as an expression vector, the nucleic acid molecule of the invention may be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (for example, region E1or E3) will result in a recombinant virus that is viable and capable of expressing the polypeptide encoded by the neculeic acid molecule of the invention in infected hosts (for example, see Logan and Shenk, *Proc. Natl. Acad. Sci. USA* 81:3655–3659, 1984). Specific initiation signals may also be required for efficient translation of inserted nucleic acid molecules. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544, 1987).

In addition, a host cell strain may be chosen which modulates the expression of the inserted sequences, or modifies and processes the gene product in the specific fashion desired. Such modifications (for example, glycosylation) and processing (for example, cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express Caspase-8h or Caspase-8i sequences described above may be engineered. Rather than using expression vectors which contain viral origins of replication, host cells can be transformed with DNA controlled by appropriate expression control elements (for example, promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which produce Caspase-8h and/or Caspase-8i. Such engineered cell lines may be particularly useful in screening and evaluation of compounds that affect the endogenous activity of the gene product.

A number of selection systems may be used, including but not limited to the herpes simplex virus thymidine kinase (Wigler, et al., *Cell* 11:223, 1977), hypoxanthine-guanine phosphoribosyltransferase (Szybalska and Szybalski, *Proc. Natl. Acad. Sci. USA* 48:2026, 1962), and adenine phosphoribosyltransferase (Lowy, et al., *Cell* 22:817, 1980) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., *Proc. Natl. Acad. Sci. USA* 77:3567, 1980; O'Hare, et al., *Proc. Natl. Acad. Sci. USA* 78:1527, 1981); gpt, which confers resistance to mycophenolic acid (Mulligan and Berg, *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al., *Gene* 30: 147, 1984).

Alternatively, any fusion protein may be readily purified by utilizing an antibody specific for the fusion protein being expressed. For example, a system described by Janknecht et al. allows for the ready purification of non-denatured fusion proteins expressed in human cell lines (*Proc. Natl. Acad. Sci. USA* 88: 8972–8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$•nitriloacetic acid-agarose columns and histidine-tagged proteins are selectively eluted with imidazole-containing buffers.

Polypeptides of the Invention

The Caspase-8h and Caspase-8i polypeptides described herein and fragments, mutants, and truncated forms thereof, including fusion proteins, can be prepared for a variety of uses, including but not limited to the generation of antibodies, as reagents in diagnostic assays, for the identification of other cellular gene products involved in the regulation of apoptosis, as reagents in assays for screening for compounds that can be used in the treatment of disorders associated with apoptotic cell death, abnormal activity of the Fas/APO-1 receptor, or abnormal activity of the TNF receptor, and as pharmaceutical reagents useful in the treatment of such disorders.

The invention encompasses proteins and polypeptides that have one or more of the functions of naturally-occurring Caspase-8h or Caspase-8i. Among the functional attributes of Caspase-8h and Caspase-8i are: the ability to bind FADD/MORT1 and the ability to inhibit cell death associated with activation of the Fas/APO1 receptor. Polypeptides having one or more functions of naturally-occurring Caspase-8h or Caspase-8i can be closely related to Caspase-8h or Caspase-8i. Such polypeptides can be created by functionally equivalent proteins include, but are not limited to, additions or substitutions of amino acid residues within the amino acid sequence encoded by the nucleotide sequences described above (see SEQ ID NOS:1 and 3), but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. Amino acids that are typically considered as providing a conservative substitution for one another are specified in the summary of the invention.

While random mutations can be made to caspase-8h or caspase-8i DNA (using random mutagenesis techniques well known to those skilled in the art) and the resulting mutant polypeptides tested for activity, site-directed mutations of these coding sequence can be engineered (using site-directed mutagenesis techniques well known to those skilled in the art) to generate mutant polypeptides with increased function, for example, higher binding affinity for FADD/MORT1, and/or greater ability to inhibit apoptotic cell death.

While the polypeptides of the invention can be chemically synthesized (for example, see Creighton, "Proteins: Structures and Molecular Principles," W. H. Freeman & Co., N.Y., 1983), large polypeptides, i.e., polypeptides equivalent in size to Caspase-8h, may advantageously be produced by recombinant DNA technology including in vitro recombinant DNA techniques, synthetic techniques, and in vivo genetic recombination described herein. In addition, skilled artisans may consult Ausubel et al. ("Current Protocols in Molecular Biology, Vol. I," Green Publishing Associates, Inc., and John Wiley & sons, Inc., N.Y., 1989), Sambrook et al. ("Molecular Cloning, A Laboratory Manual," Cold Spring Harbor Press, Cold Spring Harbor, N.Y., 1989), and, particularly for examples of chemical synthesis, Gait, M. J. (Ed. "Oligonucleotide Synthesis," IRL Press, Oxford, 1984), which are incorporated by reference herein in their entirety.

Antibodies

The invention also encompasses antibodies that bind Caspase-8h or Caspase-8i. Antibodies that specifically recognize one or more epitopes of these proteins, or fragments thereof are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of various forms of Caspase-8 in a biological sample and may, therefore, be utilized as part of a diagnostic or prognostic technique whereby patients may be tested for abnormal amounts of Caspase-8h or Caspase-8i. Such antibodies may also be utilized in conjunction with, for example, compound screening schemes, as described below, for the evaluation of the effect of test compounds on expression and/or activity of Caspase-8h or Caspase-8i. Additionally, such antibodies can be used in conjunction with the gene therapy techniques described below, to, for example, evaluate cells expressing the alternate forms described herein prior to their introduction into the patient. Preferably, the antibodies recognize epitopes of Caspase-8h or Caspase-8i that are unique, i.e., are not present on other forms of Caspase-8 or more distantly related proteins. Accordingly, the antibodies are preferably raised against a peptide sequence present in Caspase-8h or Caspase-8i that is not present in other forms of Caspase-8 (e.g., the various forms of Caspase-8 described by Boldin et al., supra).

For the production of antibodies, various host animals may be immunized by injection with a peptide having a sequence that is present in Caspase-8h and/or Caspase-8i. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein (*Nature* 256:495–497, 1975; and U.S. Pat. No. 4,376,110), the human B cell hybridoma technique (Kosbor et al., *Immunology Today* 4:72, 1983; Cole et al., *Proc. Natl. Acad. Sci. USA* 80:2026–2030, 1983), and the EBV-hybridoma technique (Cole et al., "Monoclonal Antibodies And Cancer Therapy," Alan R. Liss, Inc., pp. 77–96, 1985). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., *Proc. Natl. Acad. Sci. USA,* 81:6851–6855, 1984; Neuberger et al., *Nature,* 312:604–608, 1984; Takeda et al., *Nature,* 314:452–454, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, *Science* 242:423–426, 1988; Huston et al., *Proc. Natl. Acad. Sci. USA* 85:5879–5883, 1988; and Ward et al., 1989, *Nature* 334:544–546, 1989) can be adapted to produce single chain antibodies against caspase-8h or caspase-8i gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., *Science,* 246:1275–1281, 1989) to allow rapid and easy identification of monoclonal Fab fragments with the desired specificity.

These antibodies can, in turn, be utilized to generate anti-idiotype antibodies that "mimic" Caspase-8h or Caspase-8i, using techniques well known to those skilled in the art. (See, for example, Greenspan and Bona, *FASEB J.* 7(5):437–444, 1993; and Nissinoff, *J. Immunol.* 147(8):2429–2438, 1991). Such neutralizing anti-idiotypes or Fab fragments of such anti-idiotypes can be used in diagnostic regimens to detect disorders associated with apoptotic cell death.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., *Nature Genetics* 7:13–21, 1994; see also U.S. Pat. Nos. 5,545,806 and 5,569,825, both of which are hereby incorporated by reference).

The methods described herein may be performed, for example, by utilizing pre-packaged diagnostic kits comprising at least one specific caspase-8h or caspase-8i nucleotide sequence or antibody reagent described herein, which may be conveniently used, for example, in clinical settings, to diagnose patients exhibiting symptoms of the disorders described below.

Transgenic Animals

In another embodiment, the present invention relates to non-human, transgenic animals having cells that express the nucleic acid molecules of the invention. Preferably, the animals express Caspase-8h and/or Caspase-8i (e.g., encoded by a gene which produces Caspase-8h or Caspase-8i MRNA without splicing). Such transgenic animals represent a model system for the study of disorders that are caused by or exacerbated either by excessive or insufficient apoptotic cell death, and for the development of therapeutic agents that modulate the expression or activity of the forms of Caspase-8 described herein. As defined above, animals such as mice, rats, rabbits, guinea pigs, pigs, micro-pigs, goats, and non-human primates, for example, baboons, monkeys, and chimpanzees may be used to generate these transgenic animals.

Preferably, the transgenic animals of the present invention are produced by introducing a nucleic acid molecule of the invention into single-celled embryos so that the DNA is stably integrated into the DNA of germ-line cells in the mature animal, and inherited in a Mendelian fashion. However, any technique known in the art may be used to introduce the transgene into animals to produce the founder lines of transgenic animals. Such techniques include, but are not limited to pronuclear microinjection (see, for example, U.S. Pat. No. 4,873,191); retrovirus mediated gene transfer into germ lines (Van der Putten et al., 1985, *Proc. Natl. Acad. Sci., USA* 82:6148–6152); gene targeting in embryonic stem cells (Thompson et al., 1989, *Cell* 56:313–321); electroporation of embryos (Lo, 1983, Mol *Cell. Biol.* 3:1803–1814); and sperm-mediated gene transfer (Lavitrano et al., 1989, *Cell* 57:717–723); etc. For a review of such techniques, see Gordon, 1989, Transgenic Animals, Intl. Rev. Cytol. 115:171–229. Skilled artisans may obtain additional guidance from, for example: Hogan et al. "Manipulating the Mouse Embryo" (Cold Spring Harbor Press, Cold Spring Harbor, N.Y., 1986; Krimpenfort et al., Bio/Technology 9:86, 1991; Palmiter et al., *Cell* 41:343, 1985; Kraemer et al., "Genetic Manipulation of the Early Mammalian Embryo" (Cold Spring Harbor Press, Cold Spring Harbor, N.Y., 1985; Hammer et al., *Nature* 315:680, 1985; Purcel et al., *Science,* 244:1281, 1986; Wagner et al., U.S. Pat. No. 5,175,385; and Krimpenfort et al., U.S. Pat. No. 5,175,384 (the latter two publications are hereby incorporated by reference).

The present invention provides for transgenic animals that carry the Caspase-8-related transgene of the invention in all their cells, as well as animals which carry the transgene in some, but not all their cells, that is, the invention provides for mosaic animals. The transgene may be integrated as a single transgene or in concatamers, for example, head-to-head tandems or head-to-tail tandems. The transgene may also be selectively introduced into and activated in a particular cell type by following, for example, the teaching of Lasko et al. (*Proc. Natl. Acad. Sci. USA* 89:6232–6236, 1992). The regulatory sequences required for such a cell-type specific activation will depend upon the particular cell type of interest, and will be apparent to those of skill in the art.

When it is desired that the caspase-8h or caspase-8i transgene be integrated into the chromosomal site of the endogenous gene, gene targeting is preferred. Briefly, when such a technique is to be utilized, vectors containing some nucleotide sequences homologous to the endogenous caspase-8 gene are designed for the purpose of integrating, via homologous recombination with chromosomal sequences, into and disrupting the function of the nucleotide sequence of the endogenous caspase-8 gene. A transgene may also be selectively introduced into a particular cell type, thus inactivating or "knocking out" the endogenous gene in only that cell type, by following, for example, the teaching of Gu et al. (Science 265:103–106, 1994). The regulatory sequences required for such a cell-type specific inactivation will depend upon the particular cell type of interest, and will be apparent to those of skill in the art.

The level of MRNA expression of the transgene in the tissues of the transgenic animals may be assessed using techniques which include but are not limited to Northern blot or RNAse protection analysis of tissue samples obtained from the animal.

Use of the Nucleic Acids, Polypeptides, and Antibodies of the Invention in the Diagnosis and Treatment of Disorders Associated with Apoptotic Cell Death As described below, the nucleic acids, polypeptides, antibodies, and other reagents of the invention can be used in the diagnosis and treatment of disorders associated with apoptotic cell death. In general, disorders associated with increased cell death are those in which the expression or activity of Caspase-8h and/or Caspase-8i may be insufficient. Thus, these disorders can be treated by enhancing the expression or activity of Caspase-8h and/or Caspase-8i. Conversely, disorders associated with decreased cell death are those in which expression or activity of Caspase-8h and/or Caspase-8i is excessive, and which would respond to treatment regimes in which expression or activity of these genes is inhibited. The disorders amenable to treatment will first be briefly reviewed and a discussion of therapeutic applications will follow (see, for example, "Formulations and Use").

Skilled artisans may consult Thompson (*Science* 267:1456–1462, 1995) for a more detailed discussion of the disorders associated with apoptotic cell death.

Whether a Disorder is Mediated by the Expression of Caspase-8h or Caspase-8i

If one can determine whether a disorder is associated with apoptotic cell death, and whether that cell death is influenced by expression of the forms of Caspase-8 disclosed herein, it should be possible to determine whether that disorder can be diagnosed or treated with the nucleic acid, polypeptide, or antibody molecules of the invention. A disorder in which there is either insufficient or excessive cell death may be studied by determining whether caspase-8h or caspase-8i are either overexpressed or underexpressed in the affected tissue. The expression levels can be compared from tissue to tissue within a single patient, or between tissue samples obtained from a patient that is ill and one or more patients who are well. If it is determined that either Caspase-8h, Caspase-8i, or both are either overexpressed or underexpressed, it can be said that the disorder should be amenable to one or more of the treatment methods disclosed herein.

Diagnostic methods in which caspase-8h and caspase-8i are detected in a biological sample can be carried out, for example, by amplifying the nucleic acid molecules within the sample by PCR (the experimental embodiment set forth in Mullis, K. B., 1987, U.S. Pat. No. 4,683,202), followed by the detection of the amplified molecules using techniques well known to those of skill in the art. For example, for detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method. The resulting amplified sequences can be compared to those which were obtained either from a tissue that is not affected by the disorder, from a person who is well, or that were obtained from the patient before the disorder developed.

The level of expression of Caspase-8h and Caspase-8i can also be assayed by detecting and measuring transcription. For example, RNA from a cell type or tissue that is known, or suspected to express these forms of Caspase-8, may be isolated and tested utilizing the PCR techniques described above.

The analysis of cells taken from culture may be a necessary step in the assessment of cells to be used as part of a cell-based gene therapy technique or, alternatively, to test the effect of compounds on the expression of Caspase-8h and Caspase-8i. Such analyses may reveal both quantitative and qualitative aspects of the expression pattern of these forms of Caspase-8, including activation or inactivation of their expression.

Where a sufficient quantity of the appropriate cells can be obtained, standard Northern blot or RNAse protection analyses can be performed to determine the level of mRNA encoding the various forms of Caspase-8, particularly Caspase-8h and Caspase-8i.

It is also possible to base diagnostic assays and screening assays for therapeutic compounds on detection of Caspase-8h polypeptide or Caspase-8i polypeptide. Such assays for Caspase-8h polypeptide or Caspase-8i polypeptide, or peptide fragments thereof will typically involve incubating a sample, such as a biological fluid, a tissue extract, freshly harvested cells, or lysates of cells which have been incubated in cell culture, in the presence of a detectably labeled antibody capable of identifying these gene products (or peptide fragments thereof), and detecting the bound antibody by any of a number of techniques well-known in the art.

The biological sample may be brought in contact with and immobilized onto a solid phase support or carrier such as nitrocellulose, or other solid support which is capable of immobilizing cells, cell particles, or soluble proteins. The support may then be washed with suitable buffers followed by treatment with the detectably labeled antibody or fusion protein. The solid phase support may then be washed with the buffer a second time to remove unbound antibody or fusion protein. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-Caspase-8h or anti-Caspase-8i antibody or fusion proteins containing these polypeptides may be determined according to well known methods. Those skilled in the art will be able to determine operative and optimal assay conditions for each determination by employing routine experimentation.

With respect to antibodies, one of the ways in which the antibody of the instant invention can be detectably labeled is by linking it to an enzyme for use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, MD; Voller, A. et al., 1978, J. Clin. Pathol. 31:507–520; Butler, J. E., 1981, Meth. Enzymol. 73:482–523; Maggio, E. (ed.), "Enzyme Immunoassay," CRC Press, Boca Raton, Fla., 1980; Ishikawa, E. et al., (eds.), "Enzyme Immunoassay," Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect Caspase-8h and Caspase-8i through the use of a radioimmunoassay (RIA) (see, for example, Weintraub, B., "Principles of Radioimmunoassays, Seventh Training Course on Radioligand Assay Techniques," The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Still further, the invention encompasses methods and compositions for the treatment of the disorders described above, and any others that are found to be associated with apoptotic cell death. Such methods and compositions are capable of modulating the level of expression of caspase-8h or caspase-8i and/or the level of activity of the gene products.

Numerous ways of altering the expression or activity of the polypeptides of the invention are known to skilled artisans. For example, living cells can be transfected in vivo with the nucleic acid molecules of the invention (or transfected in vitro and subsequently administered to the patient). For example, cells can be transfected with plasmid vectors by standard methods including, but not limited to, liposome-polybrene-, or DEAE dextran-mediated transfection (see, e.g., Felgner et al., Proc. Natl. Acad. Sci. USA 84:7413, 1987; Ono et al., Neurosci. Lett. 117:259, 1990; Brigham et al., Am. J. Med. Sci. 298:278, 1989), electroporation (Neumann et al., EMBO J. 7:841, 1980), calcium phosphate precipitation (Graham et al., Virology 52:456, 1973; Wigler et al., Cell 14:725, 1978; Felgner et al., supra) microinjection (Wolff et al., Science 247:1465, 1990), or velocity driven microprojectiles ("biolistics").

These methods may be employed to mediate therapeutic application of the molecules of the invention. For example, antisense nucleic acid therapies or ribozyme approaches may be used to inhibit utilization of caspase-8h and/or caspase-8i MRNA; triple helix approaches may also be successful in inhibiting transcription of various forms of Caspase-8. Antisense approaches involve the design of oligonucleotides (either DNA or RNA) that are complementary to the mRNA molecules of the invention. The antisense oligonucleotides will bind to the complementary mRNA transcripts and prevent translation. Antisense oligonucleotides must be specific for the mRNA of interest. Accordingly, oligonucleotides spanning the splice junctions are especially preferred. For example, the following oligonucleotides are suitable for specifically binding caspase-8h MRNA: tttgtccaaagtctttgctgaatt (SEQ ID NO:7). The following oligonucleotides are suitable for specifically binding caspase-8i mRNA: tggagatttcctcttgcaaaagaaactta (SEQ ID NO:8); gatagagcatttggagatttcc (SEQ ID NO:9); and cttttcagggtaaactcaattctg (SEQ ID NO:10).

Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex. Antisense oligonucleotides complementary to mRNA coding regions are less efficient inhibitors of translation than oligonucleotides that are complementary to 5'- or 3'-untranslated sequence, but should be used in accordance with the instant invention. The antisense nucleic acids should be at least six nucleotides in length, and are preferably oligonucleotides ranging from 6 to about 50 nucleotides in length. In specific aspects, the oligonucleotide is at least 10 nucleotides, preferably at least 17 nucleotides, more preferably at least 25 nucleotides or most preferably at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotide can be modified at the base moiety, sugar moiety, or phosphate backbone, for example, to improve stability of the molecule, hybridization, etc. The oligonucleotide may include other appended groups such as peptides (for example, for targeting host cell receptors in vivo), or agents facilitating transport across the cell membrane (see, for example, Letsinger et al., *Proc. Natl. Acad. Sci. USA* 86:6553–6556, 1989; Lemaitre et al., *Proc. Natl. Acad. Sci. USA* 84:648–652, 1987; PCT Publication No. WO88/09810, published Dec. 15, 1988) or the blood-brain barrier (see, for example, PCT Publication No. WO89/10134, published Apr. 25, 1988), hybridization-triggered cleavage agents. (See, for example, Krol et al., *BioTechniques* 6:958–976, 1988) or intercalating agents (see, for example, Zon, *Pharm. Res.* 5:539–549, 1988). To this end, the oligonucleotide may be conjugated to another molecule, for example, a peptide, hybridization triggered cross-linking agent, transport agent, hybridization-triggered cleavage agent, and the like.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, *Nucl. Acids Res.* 15:6625–6641). The oligonucleotide is a 2'-0-methylribonucleotide (Inoue et al., *Nucl. Acids Res.* 15:6131–6148, 1987), or a chimeric RNA-DNA analogue (Inoue et al., *FEBS Lett.* 215:327–330, 1987).

Oligonucleotides of the invention may be synthesized by standard methods known in the art, for example, by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209,1988), methylphosphonate oligonucleotides can be prepared by use of controlled pore glass polymer supports (Sarin et al., *Proc. Natl. Acad. Sci. USA* 85:7448–7451, 1988), etc.

The antisense molecules should be delivered to cells which express caspase-8h and/or caspase-8i in vivo. A number of methods have been developed for delivering antisense DNA or RNA to cells; for example, antisense molecules can be injected directly into the tissue site, or modified antisense molecules, designed to target the desired cells (for example, antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous caspase-8h and/or caspase-8i transcripts and thereby prevent translation of the caspase-8h and/or caspase-8i MRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, *Nature* 290:304–310, 1981), the promoter contained in the 3'long terminal repeat of Rous sarcoma virus (Yamamoto et al., *Cell* 22:787–797, 1980), the herpes thymidine kinase promoter (Wagner et al., *Proc. Natl. Acad. Sci. USA* 78:1441–1445, 1981), the regulatory sequences of the metallothionein gene (Brinster et al., *Nature* 296:39–42, 1982), etc. Any type of plasmid, cosmid, YAC or viral vector can be used to prepare the recombinant DNA construct which can be introduced directly into the tissue site; for example, the choroid plexus or hypothalamus. Alternatively, viral vectors can be used which selectively infect the desired tissue; (for example, for brain, herpesvirus vectors may be used), in which case administration may be accomplished by another route (for example, systemically).

Methods of designing antisense nucleic acids and introducing them into host cells have been described in, for example, Weinberg et al. (U.S. Pat. No. 4,740,463; hereby incorporated by reference).

Alternatively, the nucleic acid molecules of the invention can be administered so that expression of the caspase-8h and/or caspase-8i occurs in tissues where it does not normally occur, or is enhanced in tissues where it is normally expressed. This application can be used, for example, to suppress apoptotic cell death and thereby treat disorders in which cellular populations are diminished, such as those described below as "disorders associated with diminished cell survival." Preferably, the therapeutic nucleic acid (or recombinant nucleic acid construct) is applied to the site where cells are at risk of dying by apoptosis, to the tissue in the larger vicinity, or to the blood vessels supplying these areas.

Ideally, the production of a polypeptide that is a form of Caspase-8 lacking the ICE/CED3 protease domain (e.g., Caspase-8h or Caspase-8i), by any gene therapy approach described herein will result in a cellular level of expression that is at least equivalent to the normal, cellular level of expression of these genes. Skilled artisans will recognize that these therapies can be used in combination with more traditional therapies, such as surgery, radiotherapy, or chemotherapy. Accordingly, and as described below, the invention features therapeutic compositions that contain the nucleic acid molecules, polypeptides, and antibodies of the invention, as well as compounds that are discovered, as described below, to affect them.

Therapeutic Compositions

The nucleic acid molecules encoding Caspase-8h and Caspase-8i, the polypeptides themselves, antibodies that specifically bind Caspase-8h and/or Caspase-8i and compounds that affect the expression or activity of Caspase-8h or Caspase-8i can be administered to a patient at therapeutically effective doses to treat or ameliorate disorders associated with apoptotic cell death. A therapeutically effective dose refers to the dose that is sufficient to result in amelioration of symptoms of disorders associated with apoptotic cell death.

Effective Dose

Toxicity and therapeutic efficacy of a given compound can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to unaffected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Levels in plasma may be measured, for example, by high performance liquid chromatography.

Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

The compounds may also be formulated in rectal compositions such as suppositories or retention enemas, for example, containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The therapeutic compositions of the invention can also contain a carrier or excipient, many of which are known to skilled artisans. Excipients which can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. The nucleic acids, polypeptides, antibodies, or modulatory compounds of the invention can be administered by any standard route of administration. For example, administration can be parenteral, intravenous, subcutaneous, intramuscular, intracranial, intraorbital, opthalmic, intraventricular, intracapsular, intraspinal, intracisternal, intraperitoneal, transmucosal, or oral. The modulatory compound can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences. It is expected that the preferred route of administration will be intravenous.

It is well known in the medical arts that dosages for any one patient depend on many factors, including the general health, sex, weight, body surface area, and age of the patient, as well as the particular compound to be administered, the time and route of administration, and other drugs being administered concurrently.

Dosages for the polypeptides and antibodies of the invention will vary, but a preferred dosage for intravenous administration is approximately 0.01 mg to 100 mg/ml blood volume. Determination of the correct dosage within a given therapeutic regime is well within the abilities of one of ordinary skill in the art of pharmacology. Skilled artisans will be aided in their determination of an adequate dosage by previous studies. For example, Abraham et al. (*J. Amer. Med. Assoc.* 273:934–941, 1995) administered TNF-αmonoclonal antibody (TNF-α-MAb) at doses ranging from 1 to 15 mg/kg. The antibody was well tolerated by all patients, even though they developed human antimurine antibodies; no serum sickness-like reactions, adverse skin reactions, or systemic allergic reactions developed. Similarly, Rankin et al. (*Br. J. Rheumatol.* 34:334–342, 1995) administered a single intravenous dose of 0.1, 1.0, or 10 mg/kg of an engineered human antibody, CDP571, which neutralizes human TNF-α. Both studies describe in detail how to evaluate patients who have been treated with antibodies.

Identification of Compounds that Mediate Oligomerization between the Fas/APO-1 or TNF Receptor Complexes and Caspase-8h and/or Caspase-8i It has been shown previously (see Background of the Invention) that apoptosis is induced by the formation of a specific complex of polypeptides, that includes Caspase-8, when either the Fas/APO-1 or TNF receptors are activated. Binding of Caspase-8h or Caspase-8i to these receptor complexes in place of forms of Caspase-8 having an ICE/CED-3 domain may inhibit apoptosis. Therefore, apoptosis can be inhibited within a cell that contains compounds that specifically promote interaction between Caspase-8h and/or Caspase-8i and proteins within the receptor complexes described above. Accordingly, the invention features a method for treating a patient who is suffering from an abnormally high rate of apoptotic cell death by administering to the patient a ligand that mediates oligomerization between proteins in either the Fas/APO-1 or TNF receptor complexes.

The invention also features methods for screening compounds to identify compounds which increase or decrease the interaction between either the Fas/APO-1 receptor complex of the TNF receptor complex and Caspase-8h or Caspase-8i. One suitable assay for determining whether Caspase-8h or Caspase-8i or some other form of Caspase-8 has associated with the Fas/APO-1 complex is an immuprecipitation assay. A suitable immunoprecipitation assay is described by Kischkel et al. (*EMBO J.* 14:5579, 1995). Anti-Caspase-8 antibodies can be used to detect various forms of Caspase-8, which can be distinguished by their size. Such assays can be performed in the presence and absence of selected compounds to identify those which increase or decrease association between a Caspase-8 and the receptor complex.

Recently, compounds that can penetrate the cell membrane were devised and shown to be capable of controlling the intracellular oligomerization of specific proteins. More specifically, ligands were used to induce intracellular oligomerization of cell surface receptors that lacked their transmembrane and extracellular regions but that contained intracellular signaling domains. Spencer et al. (*Science* 262:1019–1024, 1993) reported that addition of these ligands to cells in culture resulted in signal transmission and specific target gene activation. Further, these investigators proposed the use of these ligands "wherever precise control of a signal transduction pathway is desired." For further guidance in the use of synthetic ligands to induce dimerization of proteins, see Belshaw et al. (*Proc. Natl. Acad. Sci. USA* 93:4604–4607). This approach can be used to induce intracellular oligomerization of Caspase-8.

Identification of Compounds that Modulate the Expression or Activity of Cas ase-8h or Caspase-8i Isolation of the nucleic acid molecules described above (i.e. those encoding Caspase-8h and Caspase-8i) also facilitates the identification of compounds that can increase or decrease the expression of these molecules in vivo. To discover such compounds, cells that express Caspase-8h and/or Caspase-8i are cultured, exposed to a test compound (or a mixture of test compounds), and the level of Caspase-8h and/or Caspase-8i expression or activity is compared with the level of expression or activity in cells that are otherwise identical but that have not been exposed to the test compound(s). Many standard quantitative assays of gene expression can be utilized in this aspect of the invention. Examples of these assays are provided below.

In order to identify compounds that modulate expression of Caspase-8h or Caspase-8i (or homologous genes) the candidate compound(s) can be added at varying concentrations to the culture medium of cells that express Caspase-8h or Caspase-8i (or their homologue), as described above. These compounds can include small molecules, polypeptides, and nucleic acids. The expression of the caspases is then measured, for example, by Northern blot PCR analysis or RNAse protection analyses using a nucleic acid molecule of the invention as a probe. The level of expression in the presence of the candidate molecule, compared with the level of expression in its absence, will indicate whether or not the candidate molecule alters the expression of Caspase-8h or Caspase-8i.

Similarly, compounds that modulate the expression of the polypeptides of the invention can be identified by carrying out the assay described above and then performing a Western blot analysis using antibodies that bind Caspase-8h or Caspase-8i.

The test compounds, by altering the expression of particular isoforms of Caspase-8, will alter the ratio of Caspase-8 to Caspase-8h or Caspase-8i, or both. This, in turn, will alter the likelihood that the cell in which these molecules are expressed will undergo apoptosis. For example, if the test compound decreases the expression of Caspase-8h or Caspase-8i relative to the expression of Caspase-8, the signal generated by binding the Fas/APO or p55 receptors will be transduced, and the cell will respond by activating the apoptotic pathway. In contrast, if the test compound increases the expression of Caspase-8h or Caspase-8i relative to the expression of Caspase-8, the signal generated by binding the Fas/APO or p55 receptors will not be transduced (because the Caspase-8h and Caspase-8i isoforms lack the cysteine protease domain of the enzyme) and the cell will not undergo apoptosis. Thus, compounds identified in this way can be used as agents to control apoptosis and, in particular, as therapeutic agents for the treatment of various disorders associated with apoptosis (described above).

Compounds which alter and activity (e.g., Fas/APO-1 receptor binding, TNF receptor binding, or apoptosis inhibition) of Caspase-8h or Caspase-8i can be identified using the oligomerization and apotosis assays described in detail above.

Deposit Information

Two plasmids, cp81 and cp220, bearing cDNA encoding Caspase-8h and Caspase-8i respectively, were deposited with the American Type Culture Collection (12301 Parklawn Drive, Rockville, Md. 20852-1776) on Feb. 13, 1997. Plasmid cp81 was assigned accession number 97877, and plasmid cp220 was assigned accession number 97878.

The subject cultures have been deposited under conditions that assure that access to the cultures will be available during the pendency of the patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures plus five years after the last request for a sample from the deposit. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Additional embodiments are within the following claims.

We claim:

1. An isolated nucleic acid molecule comprising a nucleotide sequence encoding the amino acid sequence of SEQ ID NO:2.

2. An isolated nucleic acid molecule comprising a nucleotide sequence encoding the amino acid sequence of SEQ ID NO:4.

3. The nucleic acid molecule of claim 1, said molecule comprising the nucleotide sequence of SEQ ID NO:1.

4. The nucleic acid molecule of claim 2, said molecule comprising the nucleotide sequence of SEQ ID NO:3.

5. An isolated nucleic acid molecule comprising the cDNA sequence contained within the plasmid of ATCC Accession No. 97877.

6. An isolated nucleic acid molecule comprising the cDNA sequence contained within the plasmid of ATCC Accession No. 97878.

7. A vector comprising the nucleic acid molecule of claim 1, claim 2, claim 3, or claim 4.

8. The vector of claim 7, said vector being an expression vector.

9. The vector of claim 8, further comprising a regulatory element.

10. The vector of claim 9, wherein the regulatory element is selected from the group consisting of the cytomegalovirus hCMV immediate early gene, the early promoter of SV40 adenovirus, the late promoter of SV40 adenovirus, the lac system, the trp system, the TAC system, the TRC system, the major operator and promoter regions of phage λ, the control regions of fd coat protein, the promoter for 3-phosphoglycerate kinase, the promoters of acid phosphatase, and the promoters of the yeast α-mating factors.

11. The vector of claim 9, wherein said regulatory element directs tissue-specific expression.

12. The vector of claim 7, further comprising a reporter gene.

13. The vector of claim 12, wherein the reporter gene is selected from the group consisting of β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT).

14. The vector of claim 7, wherein said vector is a plasmid.

15. The vector of claim 7, wherein said vector is a virus.

16. The vector of claim 15, wherein said virus is a retrovirus.

17. A genetically engineered host cell comprising the expression vector of claim 8.

18. The cell of claim 17, wherein said cell is eukaryotic.

* * * * *